US011027036B2

(12) United States Patent
Li

(10) Patent No.: US 11,027,036 B2
(45) Date of Patent: Jun. 8, 2021

(54) ELECTRONIC SCENTED CANDLE AND FRAGRANCE CONTAINER

(71) Applicant: L&L Candle Company, LLC, Brea, CA (US)

(72) Inventor: Xiaofeng Li, Shenzhen (CN)

(73) Assignee: L&L Candle Company, LLC, Brea, CA (US)

( * ) Notice: Subject to any disclaimer, the term of this patent is extended or adjusted under 35 U.S.C. 154(b) by 0 days.

(21) Appl. No.: 17/141,923

(22) Filed: Jan. 5, 2021

(65) Prior Publication Data

US 2021/0121594 A1 Apr. 29, 2021

Related U.S. Application Data

(63) Continuation of application No. 16/376,835, filed on Apr. 5, 2019, which is a continuation of application (Continued)

(30) Foreign Application Priority Data

Jun. 17, 2017 (CN) .......................... 201710461749.X

(51) Int. Cl.
*A61L 9/00* (2006.01)
*A61L 9/03* (2006.01)
(Continued)

(52) U.S. Cl.
CPC ................. *A61L 9/03* (2013.01); *A61L 9/032* (2013.01); *A61L 9/037* (2013.01); *F21S 9/02* (2013.01);
(Continued)

(58) Field of Classification Search
CPC .. A61L 9/03; A61L 9/037; A61L 9/032; F21S 9/02; F21S 10/043
See application file for complete search history.

(56) References Cited

U.S. PATENT DOCUMENTS

| 782,156 A | 2/1905 | Meeker |
| 817,772 A | 4/1906 | Helmer |

(Continued)

FOREIGN PATENT DOCUMENTS

| CA | 2987668 | 6/2018 |
| CN | 1030823 | 2/1989 |

(Continued)

OTHER PUBLICATIONS

Canadian Examination and Search Report for CA2936224, dated Sep. 30, 2016, 5 pages.
(Continued)

*Primary Examiner* — Tracie Y Green
(74) *Attorney, Agent, or Firm* — Perkins Coie LLP

(57) ABSTRACT

An electronic scented candle is described that includes a movable flame-shaped component, a shell including an installation chamber, a fragrance container that is removably positioned inside the installation chamber and a scent chamber. An electric fan is positioned within the shell to drive the air into the scent chamber and a scent outlet coupled to the scent chamber to allow the fragrance material to leave the scent chamber and to reach an external environment of the electronic scented candle. The electronic candle also includes a receptacle for connecting a power cord on a bottom surface of the electronic candle. The bottom surface includes a plurality of protruding stands that provide a space to allow the power cord to be connected to the receptacle and be routed below the bottom surface.

29 Claims, 17 Drawing Sheets

Related U.S. Application Data

No. 16/027,124, filed on Jul. 3, 2018, now Pat. No. 10,251,968, which is a continuation of application No. 15/705,133, filed on Sep. 14, 2017, now Pat. No. 10,010,640.

(51) Int. Cl.
- *F21S 10/04* (2006.01)
- *F21S 9/02* (2006.01)
- *F21W 121/00* (2006.01)

(52) U.S. Cl.
CPC ......... *F21S 10/043* (2013.01); *A61L 2209/12* (2013.01); *A61L 2209/133* (2013.01); *A61L 2209/135* (2013.01); *A61L 2209/15* (2013.01); *F21W 2121/00* (2013.01)

(56) References Cited

U.S. PATENT DOCUMENTS

| | | |
|---|---|---|
| 1,507,371 A | 8/1924 | Goodridge |
| 1,842,167 A | 1/1932 | Hall |
| 1,955,042 A | 4/1934 | Work |
| D102,561 S | 12/1936 | Lamb |
| 2,435,811 A | 2/1948 | Waters |
| 2,932,351 A | 6/1958 | Bried |
| 2,976,450 A | 3/1961 | Benoliel |
| 2,984,032 A | 5/1961 | Cornell |
| 3,233,093 A | 2/1966 | Gerlat |
| 3,384,774 A | 5/1968 | English |
| 3,425,157 A | 2/1969 | Hartsock |
| 3,514,660 A | 5/1970 | Kopelman |
| 3,603,013 A | 9/1971 | Gardiner |
| 3,639,749 A | 2/1972 | Beckman |
| 3,681,588 A | 8/1972 | Lee |
| 3,814,973 A | 6/1974 | Thouret et al. |
| 3,890,085 A | 6/1975 | Andeweg |
| 4,026,544 A | 5/1977 | Plambeck et al. |
| 4,067,111 A | 1/1978 | Truitt |
| 4,328,534 A | 5/1982 | Abe |
| 4,477,249 A | 10/1984 | Ruzek et al. |
| 4,550,363 A | 10/1985 | Sandell |
| 4,551,794 A | 11/1985 | Sandell |
| 4,617,614 A | 10/1986 | Lederer |
| 4,728,871 A | 3/1988 | Andrews |
| 4,777,571 A | 10/1988 | Morgan |
| 4,866,580 A | 9/1989 | Blackerby |
| 4,965,707 A | 10/1990 | Butterfield |
| 4,968,487 A | 11/1990 | Yamamoto |
| 5,072,208 A | 12/1991 | Christensen |
| 5,097,180 A | 3/1992 | Ignon et al. |
| 5,152,602 A | 10/1992 | Boschetto |
| 5,381,325 A | 1/1995 | Messana |
| 5,707,282 A | 1/1998 | Clements et al. |
| 5,924,784 A | 7/1999 | Chliwnyj et al. |
| 6,198,229 B1 | 3/2001 | McCloud |
| 6,241,362 B1 | 6/2001 | Morrison |
| 6,257,755 B1 | 7/2001 | Sevelle |
| 6,302,555 B1 | 10/2001 | Bristow |
| 6,312,137 B1 | 11/2001 | Hsieh |
| 6,454,425 B1 | 9/2002 | Lin |
| 6,461,011 B1 | 10/2002 | Harrison |
| 6,511,219 B2 | 1/2003 | Sevelle |
| D486,924 S | 2/2004 | Skradski et al. |
| 6,688,752 B2 | 2/2004 | Moore |
| 6,712,493 B2 | 3/2004 | Tell et al. |
| 6,757,487 B2 | 6/2004 | Martin et al. |
| 6,781,270 B2 | 8/2004 | Long |
| 6,953,401 B2 | 10/2005 | Starr |
| 6,955,440 B2 | 10/2005 | Niskanen |
| 6,966,665 B2 | 11/2005 | Limburg et al. |
| 7,029,146 B2 | 4/2006 | Kitchen |
| 7,066,637 B2 | 6/2006 | Nozawa |
| 7,080,472 B2 | 7/2006 | Schroeter et al. |
| 7,080,762 B1 | 7/2006 | Schwartz et al. |
| 7,083,315 B2 | 8/2006 | Hansler et al. |
| 7,093,949 B2 | 8/2006 | Hart et al. |
| 7,111,421 B2 | 9/2006 | Corry et al. |
| 7,118,243 B2 | 10/2006 | McCavit et al. |
| 7,125,142 B2 | 10/2006 | Wainwright |
| 7,159,994 B2 | 1/2007 | Schnuckle et al. |
| D545,458 S | 6/2007 | Jensen |
| 7,261,455 B2 | 8/2007 | Schnuckle et al. |
| 7,300,179 B1 | 11/2007 | LaDuke et al. |
| 7,305,783 B2 | 12/2007 | Mix et al. |
| D567,993 S | 4/2008 | Shiu |
| 7,350,720 B2 | 4/2008 | Jaworksi |
| 7,360,935 B2 | 4/2008 | Jensen et al. |
| D576,317 S | 9/2008 | Jensen |
| D589,176 S | 3/2009 | Huang et al. |
| D599,491 S | 9/2009 | Luo |
| 7,633,232 B2 | 12/2009 | Wong |
| 7,686,471 B2 | 3/2010 | Reichow |
| 7,695,171 B2 | 4/2010 | Lederer |
| 7,723,899 B2 | 5/2010 | Blandino |
| 7,784,959 B2 | 8/2010 | Yang |
| 7,824,627 B2 | 11/2010 | Michaels et al. |
| 7,828,462 B2 | 11/2010 | Jensen et al. |
| 7,837,355 B2 | 11/2010 | Schnuckle |
| 8,070,319 B2 | 12/2011 | Schnuckle et al. |
| 8,081,872 B2 | 12/2011 | Wang |
| 8,132,936 B2 | 3/2012 | Patton et al. |
| 8,210,708 B2 | 7/2012 | Negron |
| 8,235,558 B1 | 8/2012 | Lauer |
| 8,256,935 B1 | 9/2012 | Cullimore et al. |
| 8,342,712 B2 | 1/2013 | Patton |
| 8,412,029 B2 | 4/2013 | Browder |
| 8,454,190 B2 | 6/2013 | Negron |
| 8,534,869 B2 | 9/2013 | Patton et al. |
| 8,579,461 B2 | 11/2013 | Fournier |
| 8,628,223 B2 | 1/2014 | Kwok |
| 8,696,166 B2 | 4/2014 | Patton et al. |
| 8,789,986 B2 | 7/2014 | Li |
| 8,878,442 B2 | 11/2014 | Lu |
| 8,894,261 B2 | 11/2014 | Chen |
| 8,926,137 B2 | 1/2015 | Li |
| 8,960,975 B2 | 2/2015 | Yang |
| 8,998,461 B2 | 4/2015 | Gutstein et al. |
| D729,424 S | 5/2015 | Li |
| 9,033,533 B2 | 5/2015 | Li |
| 9,033,553 B2 | 5/2015 | Li |
| 9,052,078 B2 | 6/2015 | Sheng |
| 9,068,706 B2 | 6/2015 | Fournier |
| D739,573 S | 9/2015 | Li |
| 9,133,992 B2 | 9/2015 | Lee |
| D744,128 S | 11/2015 | Li |
| 9,185,199 B2 | 11/2015 | Zurek |
| D748,298 S | 1/2016 | Li |
| 9,322,523 B2 | 4/2016 | Patton |
| D757,306 S | 5/2016 | Li |
| D757,335 S | 5/2016 | Li |
| D757,336 S | 5/2016 | Li |
| D757,337 S | 5/2016 | Li |
| 9,335,014 B2 | 5/2016 | Li |
| D759,858 S | 6/2016 | Li |
| D759,879 S | 6/2016 | Li |
| D759,880 S | 6/2016 | Li |
| D760,405 S | 6/2016 | Li |
| D760,422 S | 6/2016 | Li |
| D760,423 S | 6/2016 | Li |
| D760,424 S | 6/2016 | Li |
| 9,360,181 B2 | 6/2016 | Li |
| 9,366,402 B2 | 6/2016 | Li |
| 9,371,972 B2 | 6/2016 | Li |
| 9,371,973 B2 | 6/2016 | Li |
| D763,479 S | 8/2016 | Li |
| D767,799 S | 9/2016 | Li |
| D767,810 S | 9/2016 | Li |
| 9,447,938 B2 | 9/2016 | Li |
| D774,474 S | 12/2016 | Li |
| D774,478 S | 12/2016 | Li |
| 9,512,971 B2 | 12/2016 | Li |
| 9,518,710 B2 * | 12/2016 | Li ...................... F21V 33/0092 |
| 9,523,471 B2 | 12/2016 | Li |

(56) References Cited

U.S. PATENT DOCUMENTS

| | | |
|---|---|---|
| 9,551,470 B2 | 1/2017 | Li |
| 9,572,236 B2 | 2/2017 | Patton |
| 9,574,748 B2 | 2/2017 | Dong |
| 9,585,980 B1 | 3/2017 | Li |
| 9,591,727 B2 | 3/2017 | Kim |
| 9,605,824 B1 | 3/2017 | Li |
| 9,625,112 B2 | 4/2017 | Li |
| D789,570 S | 6/2017 | Li |
| D790,749 S | 6/2017 | Li |
| D791,391 S | 7/2017 | Li |
| D791,392 S | 7/2017 | Li |
| D792,634 S | 7/2017 | Li |
| 9,702,517 B2 | 7/2017 | Patton |
| D795,735 S | 8/2017 | Li |
| 9,739,432 B2 | 8/2017 | Li |
| 9,752,740 B1 | 9/2017 | Li |
| D800,929 S | 10/2017 | Li |
| D802,180 S | 11/2017 | Li |
| 9,810,388 B1 | 11/2017 | Li |
| 9,860,953 B2 | 1/2018 | Li |
| 9,869,439 B2 | 1/2018 | Li |
| 10,010,640 B1* | 7/2018 | Li ............... F21S 10/043 |
| 10,111,307 B2 | 10/2018 | Li |
| 10,251,968 B2* | 4/2019 | Li ............... F21S 10/043 |
| 10,330,300 B2 | 6/2019 | Li |
| 10,539,301 B2* | 1/2020 | Li ............... F21S 6/001 |
| 2002/0158351 A1 | 10/2002 | Wohrle |
| 2003/0198045 A1 | 10/2003 | Kitchen |
| 2004/0264169 A1* | 12/2004 | Limburg ......... A61L 9/127 |
| | | 362/96 |
| 2007/0217771 A1 | 9/2007 | Granger et al. |
| 2010/0284168 A1 | 11/2010 | Walter et al. |
| 2014/0140042 A1 | 5/2014 | Schreiber |
| 2016/0290580 A1 | 10/2016 | Li |
| 2017/0122541 A1* | 5/2017 | Patton ............. A61L 9/014 |
| 2017/0191632 A1 | 7/2017 | Li |
| 2017/0274405 A1 | 9/2017 | Lucas et al. |
| 2017/0307223 A1 | 10/2017 | Li |
| 2020/0069830 A1* | 3/2020 | Li ............... A61L 9/03 |

FOREIGN PATENT DOCUMENTS

| | | |
|---|---|---|
| CN | 2483103 | 3/2002 |
| CN | 2551859 | 5/2003 |
| CN | 2562059 Y | 7/2003 |
| CN | 1530142 A | 9/2004 |
| CN | 1646177 A | 7/2005 |
| CN | 2854329 Y | 1/2007 |
| CN | 2888274 Y | 4/2007 |
| CN | 200940808 Y | 8/2007 |
| CN | 201011621 Y | 1/2008 |
| CN | 201059432 Y | 5/2008 |
| CN | 201093300 | 7/2008 |
| CN | 201103952 Y | 8/2008 |
| CN | 201159425 Y | 12/2008 |
| CN | 101408284 A | 4/2009 |
| CN | 201235095 Y | 5/2009 |
| CN | 201418887 Y | 3/2010 |
| CN | 201533921 U | 7/2010 |
| CN | 101865413 A | 10/2010 |
| CN | 201643048 U | 11/2010 |
| CN | 102147095 A | 8/2011 |
| CN | 102748589 A | 10/2012 |
| CN | 203131550 | 8/2013 |
| CN | 203273670 U | 11/2013 |
| CN | 203442498 U | 2/2014 |
| CN | 203517611 U | 4/2014 |
| CN | 203571618 U | 4/2014 |
| CN | 104048246 | 9/2014 |
| CN | 104089241 | 10/2014 |
| CN | 203940346 | 11/2014 |
| CN | 204268356 | 4/2015 |
| DE | 1489617 A1 | 5/1969 |
| DE | 212011100014 U1 | 4/2012 |
| DE | 202015000490 U1 | 3/2013 |
| DE | 102012206988 A1 | 10/2013 |
| DE | 202013012047 U1 | 2/2015 |
| DE | 202015102274 U1 | 5/2015 |
| EP | 138786 A1 | 4/1985 |
| EP | 855189 A2 | 7/1998 |
| EP | 1838110 A1 | 9/2007 |
| EP | 1639291 B1 | 5/2009 |
| EP | 2587127 A1 | 5/2013 |
| GB | 2230335 | 10/1990 |
| GB | 2267746 | 12/1993 |
| GB | 2323159 A | 9/1998 |
| GB | 2379731 A | 3/2003 |
| GB | 2385413 A | 8/2003 |
| GB | 2443926 | 5/2008 |
| GB | 2455598 A | 6/2009 |
| GB | 2527626 | 12/2015 |
| JP | H0652709 | 2/1994 |
| JP | H1057464 A | 3/1998 |
| JP | 10-263066 | 10/1998 |
| JP | 2000284730 A | 10/2000 |
| JP | 200818075 A | 8/2008 |
| KR | 2017096663 | 8/2017 |
| WO | WO1982002756 A1 | 8/1982 |
| WO | WO1985003561 A1 | 8/1985 |
| WO | WO1987004506 A1 | 7/1987 |
| WO | WO1996025624 A1 | 8/1996 |
| WO | WO2001092780 | 12/2001 |
| WO | WO2003011349 | 2/2003 |
| WO | WO2006020839 A2 | 2/2006 |
| WO | WO2008092753 A2 | 8/2008 |
| WO | WO2010009575 | 1/2010 |
| WO | WO2012000418 A1 | 1/2012 |
| WO | WO2012099718 A1 | 7/2012 |
| WO | WO2013020263 A2 | 2/2013 |
| WO | WO2013020439 | 2/2013 |
| WO | WO2014139483 A1 | 9/2014 |
| WO | WO 2016000517 | 1/2016 |
| WO | WO 2017069328 | 4/2017 |

OTHER PUBLICATIONS

Canadian Examination and Search Report for CA2936225, dated Sep. 29, 2016, 5 pages.
Canadian Examination Report issued for Canadian Patent Application No. 2930099, dated Jan. 5, 2017.
Canadian Examination Report issued for Canadian Patent Application No. 2930099, dated Aug. 15, 2016.
Definition of "Electromagnet" in the Encarta World English Dictionary, Aug. 1999.
Engineer's Handbook (Epoxy definition), http://engineershandbook.com/Materials/epoxy.htm, Jul. 18, 2013.
EP Search Report for European Patent Application No. 12185984.7 dated Dec. 14, 2012.
German Office Action issued for German Patent Application No. 102016008225.9, dated Dec. 19, 2016.
German Office Action issued for German Patent Application No. 102016008825.7, dated Mar. 20, 2017.
International Search Report and Written Opinion for PCT Application No. PCT/CN/2014/073557 dated Jul. 2, 2014.
International Search Report for PCT Application No. PCT/US2009/054401 dated Oct. 26, 2009.
International Search Report for PCT/CN2014/091362 dated Apr. 3, 2015, 2 pages.
Lab M3: The Physical Pendulum, Physics 1140—Experimental Physics, Course Laboratory Instructions, 2000.
Nagashima, H. et al., "Introduction to Chaos, Physics and Mathematics of Chaotic Phenomena," Institute of Physics Publishing, 1999.
Supplementary Search Report and Opinion for EP 14764844, dated Jul. 28, 2016, 12 pages.
UK Combined Search and Examination Report for GB1613387.8, dated Sep. 9, 2016, 10 pages.
UK Combined Search and Examination Report for GB1613391.0, dated Sep. 19, 2016, 9 pages.

(56) References Cited

OTHER PUBLICATIONS

UK Combined Search and Examination Report for GB1613393.6, dated Sep. 9, 2016, 10 pages.

* cited by examiner

ELECTRONIC SCENTED CANDLE AND FRAGRANCE CONTAINER

RELATED APPLICATIONS

This patent document is a continuation of U.S. patent application Ser. No. 16/376,835, filed on Apr. 5, 2019, which is a continuation of U.S. patent application Ser. No. 16/027,124, filed Jul. 3, 2018, now U.S. Pat. No. 10,251,968, which is a continuation of U.S. patent application Ser. No. 15/705,133, filed Sep. 14, 2017, now U.S. Pat. No. 10,010,640, which claims priority to Chinese Patent Application No. 201710461749.X, filed Jun. 17, 2017. The entire contents of the before mentioned patent applications are incorporated by reference in this patent document.

FIELD OF THE INVENTION

The disclosed technology relates to electronic scented candles and fragrance containers associated therewith.

DESCRIPTION OF THE RELATED ART

Candles are used in many settings, such as in households, in public restaurants, churches, temples, large theme parks and even urban public infrastructures. Due to their short lifetime, however, conventional candles need to replaced frequently. In addition, open flame of a real candle can be a potential fire hazard, which also limits the extent to which candles are used.

Along with the development of new technologies, scented candles that are electrically powered have appeared in the market. These electronic scented candles simulate a flickering flame, which plays a great role in creating the proper atmosphere for the above venues and household environments. In addition to their use as a decorative piece, these candles can provide additional practical functions such as releasing a scent by using a fan that forces the scent to a scent outlet for release into an external environment. However, such a electronic scented candles often do not produce a satisfactory scent, and are not convenient to use.

SUMMARY OF THE INVENTION

The disclosed technology relates to an electronic scented candle that is convenient to use and enable rapid generation and dissipation of scented material.

One aspect of the disclosed technology relates to an electronic scented candle that includes a flame piece, a shell including an installation chamber, a fragrance container that is removably positioned inside the installation chamber, a scent chamber, and a liquid suction channel positioned within the fragrance container, where a first end of the liquid suction channel protrudes from the fragrance container into the scent chamber and a second end of the liquid suction channel is positioned within the fragrance container to draw a fragrance material from the fragrance container to the scent chamber. The electronic scented candle further includes a scent outlet in communication with the scent chamber to allow scent from the scent chamber to reach an external environment of the electronic scented candle, and an air inlet in communication with the scent chamber to direct air from the external environment to the scent chamber. The electronic scented candle also includes a heating device in communication with the scent chamber to provide thermal energy to the fragrance material drawn into the scent chamber and to the external air drawn into the scent chamber through the air inlet. The the heating device is configured to impart the thermal energy to contents of the scent chamber and to volatize the contents of the scent chamber.

DETAILED DESCRIPTION OF THE INVENTION

Figure 1A:
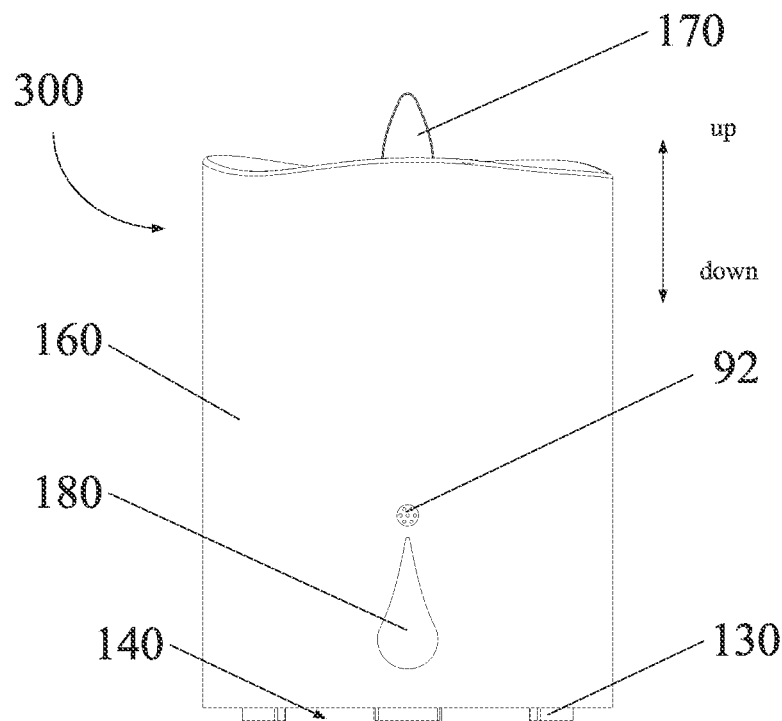
FIG. 1A illustrates an electronic scented candle according to an exemplary embodiment.

As shown in FIG. 1A through FIG. 6B, an electronic scented candle 300 according to an embodiment of the disclosed technology comprises a shell 160, a fragrance container 10, a scent chamber 20, a liquid suction channel 30, and a heating device 40. In particular, FIG. 1A illustrates a side view of the electronic scented candle 300 having a shell 160, and further illustrating a observation window 180 and a sound sensor 92, which will be discussed in further detail in the following sections. FIG. 1A also shows a flame piece 170 and support components 130 (or legs), which allow the candle device to be placed on a flat surface while maintaining the desired distance or spacing 140 between the bottom of the candle and the surface that it is placed upon.

Figure 1B:
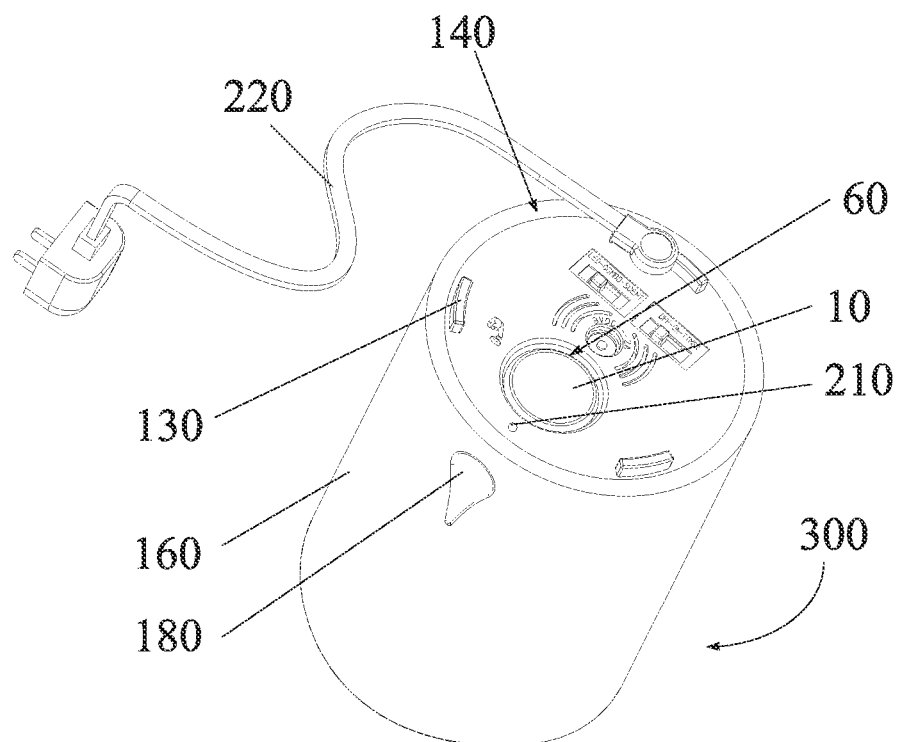
FIG. 1B illustrates another exemplary view of an electronic scented candle according to an exemplary embodiment.
Figure 1C:
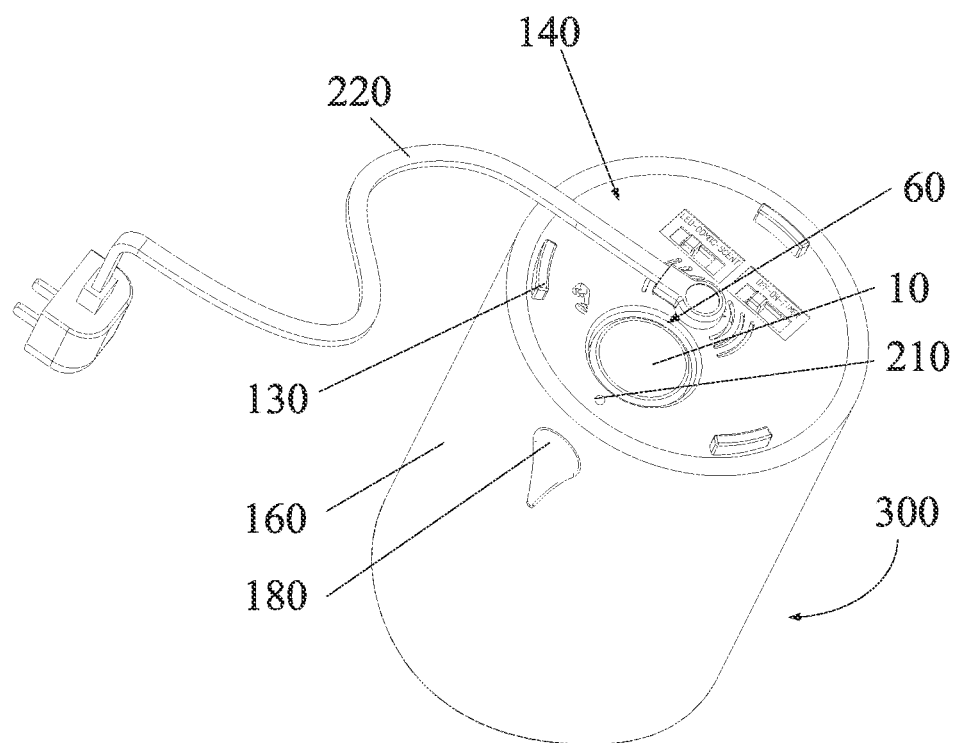
FIG. 1C illustrates an electronic scented candle according to an exemplary embodiment that includes an electric cord.

FIG. 1B illustrates some of the components of the electronic scented candle 300 when the candle 300 is turned upside down, including on/off/timer switches, a power cord 220 and a prompt point 210 (which will be described in further detail below). FIG. 1B also shows a gap 60 between the fragrance container 10 and the wall of the installation chamber that accommodates the fragrance container. FIG. 1C is similar to FIG. 1B but with an end of the power cord 220 connected to the receptacle at the center of the bottom section of the electronic scented candle 300. It should be noted that the power cord is provided additionally or alternatively to the embodiment that is shown in FIG. 1A.

Figure 1D:
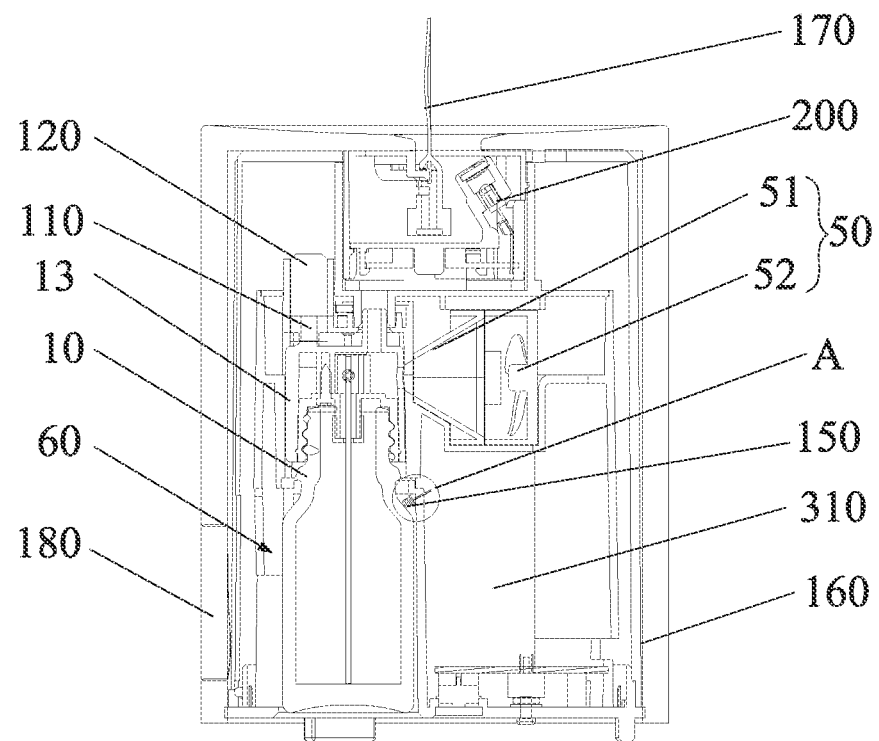
FIG. 1D illustrates a cross-sectional view of an electronic scented candle according to an exemplary embodiment.

FIG. 1D illustrates some of the internal components and their locations within the scented electronic candle 300, including a light-emitting element 200 that illuminates the flame piece 170, an additional light source 150, a buckle 110 and a slot 120 (both of which will be described further), and an air supply assembly 50 that includes a hood 51 and a fan 52. FIG. 1D also shows one or more batteries 310. The section in FIG. 1D that is identified by the letter A is magnified and shown in FIG. 1E, further illustrating the positioning of the additional light source 150 with respect to a section of the fragrance container body 12.

Figure 4A:
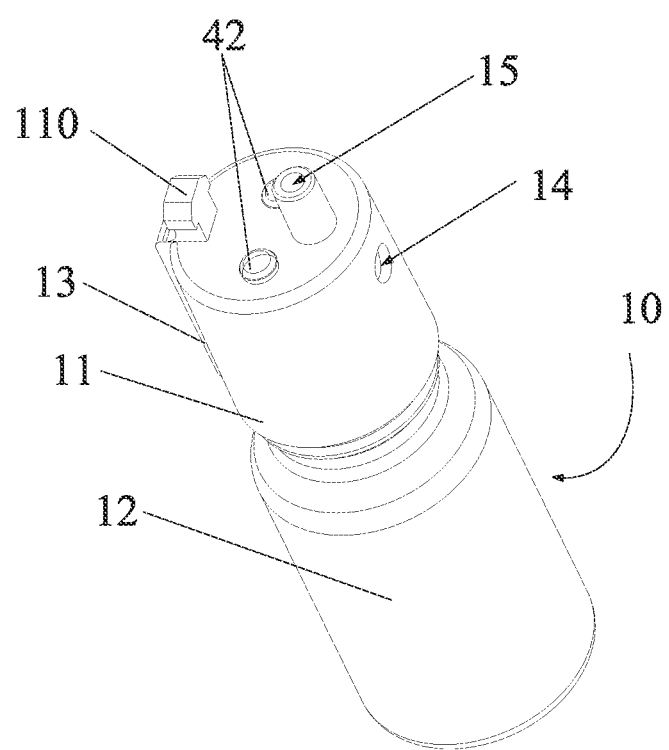
FIG. 4A illustrates a fragrance container in accordance with an exemplary embodiment.

Specifically, the shell comprises an installation chamber and a scent outlet. There may also be a plurality of scent outlets such that a scent is rapidly diffused into the air. In one embodiment, the hole on the top of the electronic scented candle 300 that allows the flame piece 170 to extend outward is the same hole as the scent outlet. Additionally, or alternatively, the scent outlet may be formed separately, for example, on the side or bottom of the electronic scented candle 300. The fragrance container 10 is installed inside the installation chamber. As illustrated in, for example, FIGS. 4A and 4F, a vent hole 15 of the scent chamber 20 is in communication with the scent outlet, and an air inlet 14 of the scent chamber 20 is in communication with the external air (e.g., the air outside of the scented candle device 300 that is drawn into the air inlet 14). Various components and views of the fragrance container 10 are shown in FIGS. 4A to 5A. For example, as seen in FIGS. 4D and 4F, one end of the liquid suction channel 30 extends into a fragrance liquid in the fragrance container 10, while the other end of the liquid suction channel 30 extends into the scent chamber 20. The liquid suction channel 30 is capable of sucking fragrance from one end of the liquid suction channel 30 to the other end thereof. As shown in, for example, FIGS. 4B and 5A, a heating device 40 is disposed inside the scent chamber 20 for heating the other end of the liquid suction channel 30.

In operation, a liquid in the fragrance container 10 rises from the bottom to the top of the liquid suction channel 30 due to, e.g., capillary action, the heating device 40 heats the liquid suction channel 30 to accelerate volatilization of the fragrance that is dispersed to the external environment (external environment refers to the environment outside of the electronic scented candle 300). Heat can accelerate the movement speed of the molecules, and the heated fragrance molecules can move into the air rapidly such that the electronic scented candle 300 can quickly produce a scent after operation.

Figure 4B:
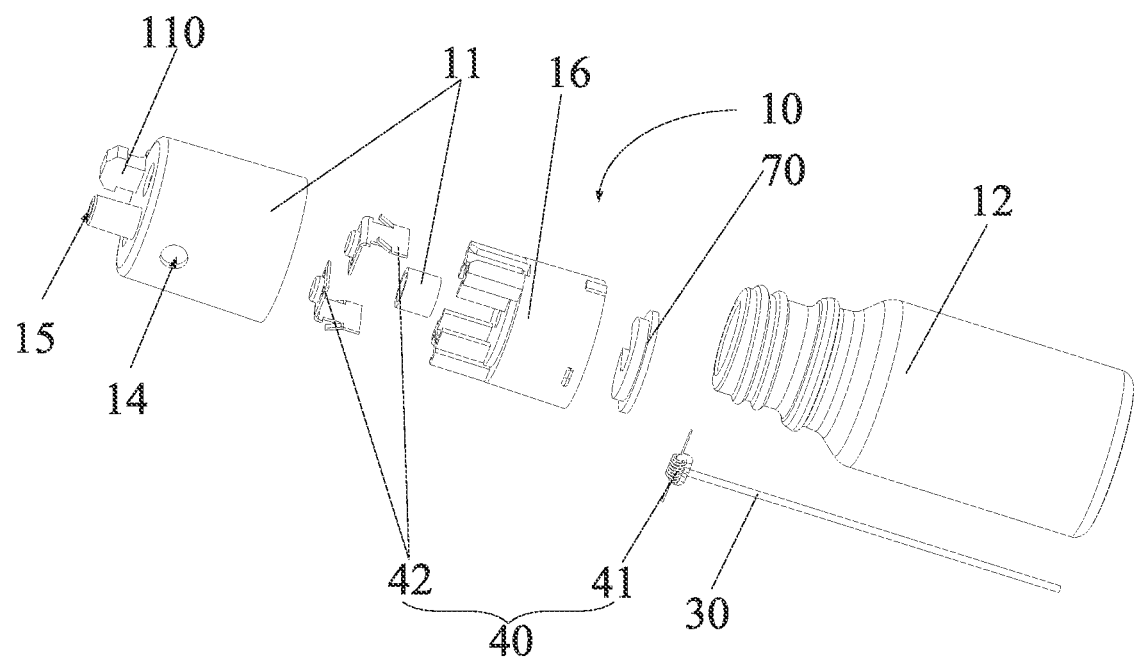
FIG. 4B illustrates an exploded view of a fragrance container in accordance with an exemplary embodiment.
Figure 4C:
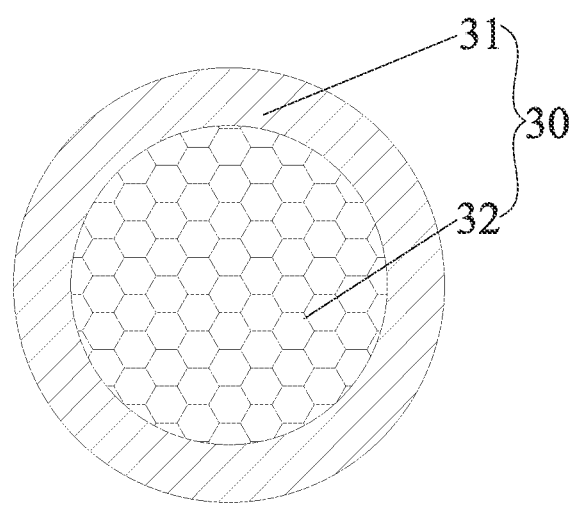
FIG. 4C illustrates a cross-sectional view of a liquid suction channel in accordance with an exemplary embodiment.
Figure 4D:
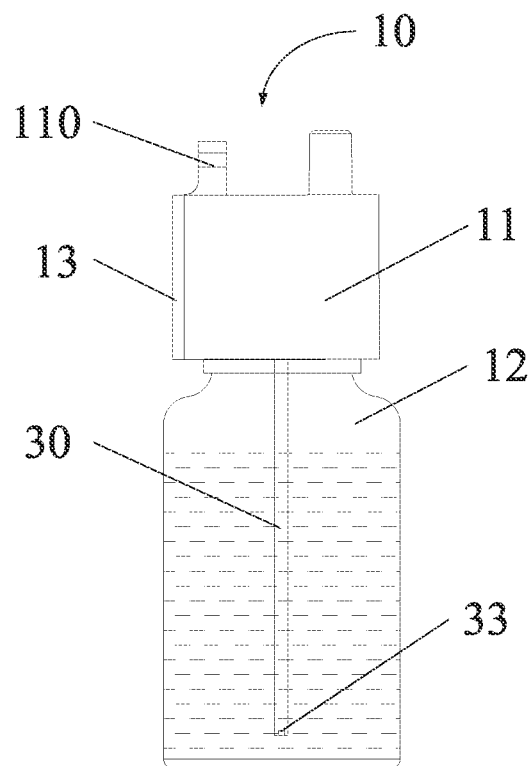
FIG. 4D illustrates a fragrance container in an upright position in accordance with an exemplary embodiment.
Figure 4E:
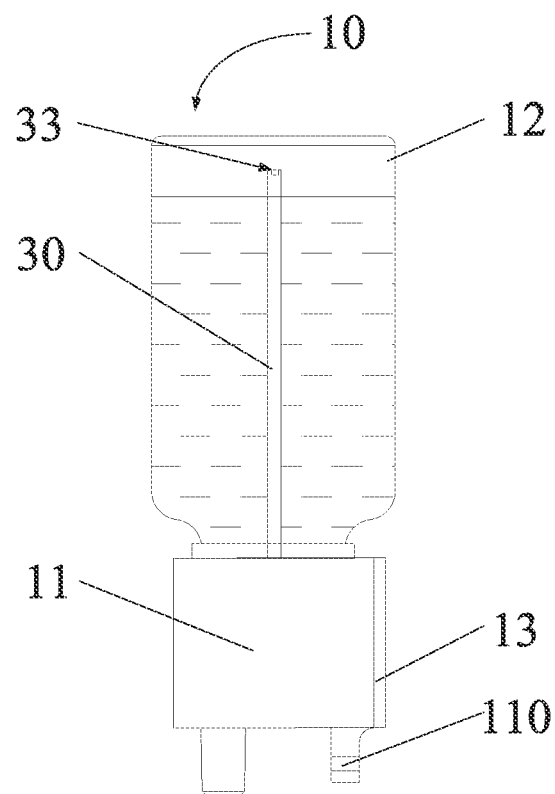
FIG. 4E illustrates a fragrance container in an upside down position in accordance with an exemplary embodiment.
Figure 4F:
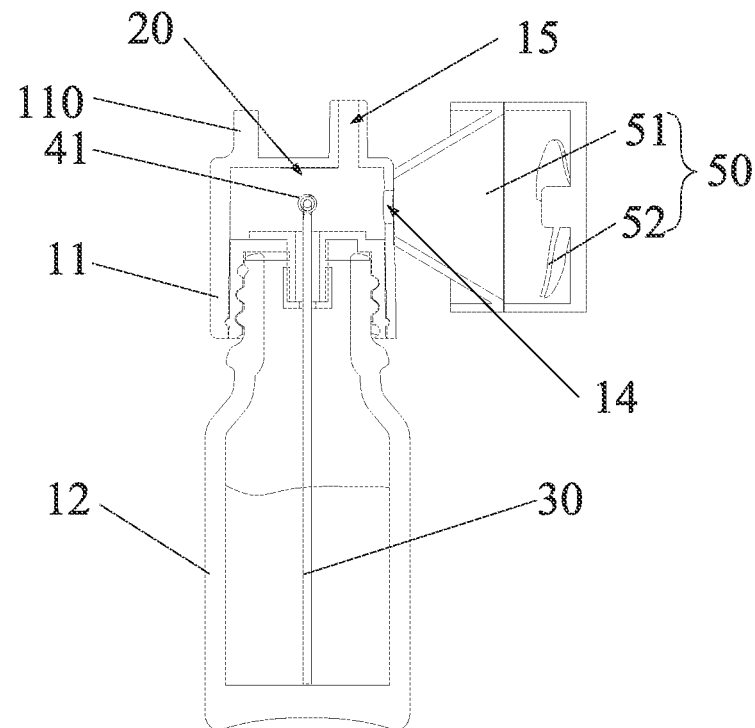
FIG. 4F illustrates a fragrance container and an air supply assembly in accordance with an exemplary embodiment.
Figure 5A:
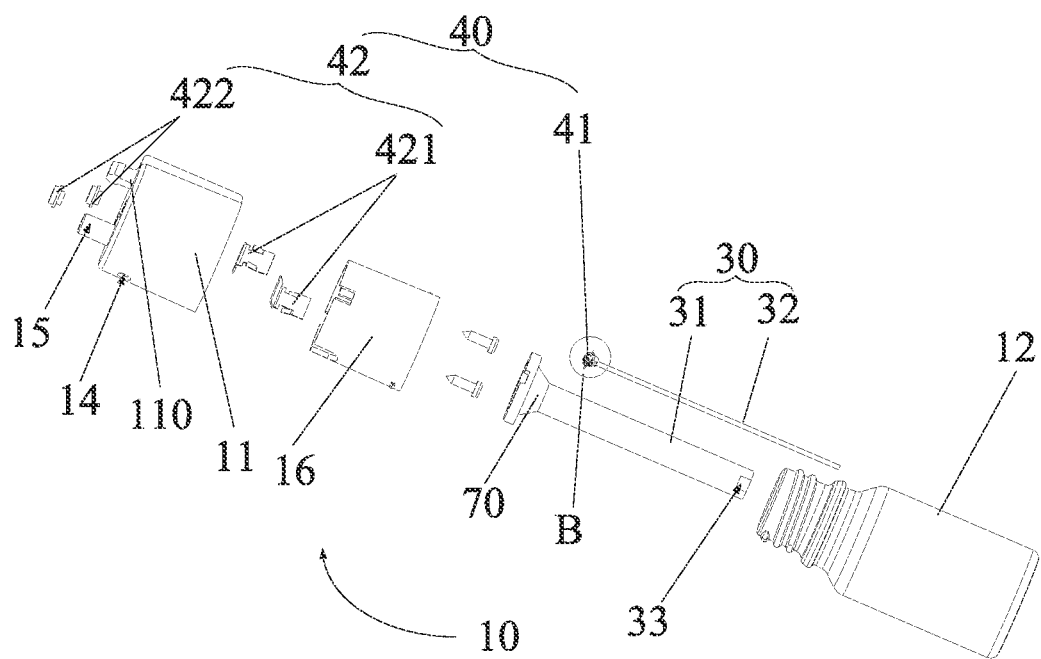
FIG. 5A illustrates an exploded view of a fragrance container in accordance with an exemplary embodiment.

In some embodiments, as shown in FIGS. 4B, 4F and 5A, the fragrance container 10 comprises a cover body 11 and a bottle body 12. The scent chamber 20 (see FIG. 4F) is formed within the cover body 11. It is understood that the scent chamber 20 may also be formed at other positions of the electronic scented candle 300. The cover body 11 includes one or more air inlets 14 that are in communication with the external air via an air supply channel that cause outside air to flow into the scent chamber 20. The fragrance is heated and turned into gas in the scent chamber 20, it is mixed with the air that is already in the scent chamber 20 (or is subsequently received by the scent chamber 20) and is then disseminated to the external environment though the scent outlet. The external air enters the scent chamber via the air supply channel and the air inlets to replenish the air in the scent chamber 20. In one embodiment, the shell of the cover body 11 is made of a high temperature-resistant material to delay the aging process of the cover body 11 and to therefore extend the useful life of the cover body 11. In one embodiment, the diameter of the air inlet 14 tapers in a direction of air flow; for example, the air inlet 14 is funnel shaped such that the air flowing out of the air inlet 14 has a higher velocity relative to the air at the flows into the air inlet 14. The air flow accelerates volatilization of the fragrance at the upper end of the liquid suction channel 30 causing the fragrance material to be volatilized and rapidly dispersed into the external environment.

In some embodiments, the electronic scented candle further comprises a temperature controller. The temperature controller can control the on and off operation of the heating device. When the electronic scented candle just begins to work, the temperature controller controls the heating device to increase the temperature rapidly. For example, the temperature of the heating device can rapidly increase to about 280° C. to 300° C., thus enabling the fragrance material at the other end of the liquid suction channel to be rapidly volatilized and dispersed into the outside environment. When the electronic scented candle has worked for a period of time, for example, 10 to 20 minutes, the temperature of the heating device is lowered. For example, the temperature of the heating device is lowered to 200° C. to 250° C., which reduces the volatilization rate of the fragrance material. When the electronic scented candle has worked for another period of time, e.g. 30 to 60 minutes, the temperature of the heating device is further lowered. For example, the temperature of the heating device is lowered to 150° C. to 180° C. such that the fragrance is volatilized slowly and continuously into the air. The above control method keeps the fragrance content of the environment surrounding the scented candle within a reasonable range and avoids situations in which the scent is too strong, or is intermittent. In some embodiments, the temperature of the heating device is in a range of 170° C. to 230° C. When a fragrance material is heated to the above temperature range, the fragrance can be fully turned into a gaseous form having very fine particles, which enables the fragrance to be rapidly and evenly dispersed in to the air.

In some embodiments, the fragrance container may also be filled with pure water, allowing a user to select a humidification mode of operation associated with the electronic scented candle. In such embodiments, the electronic scented candle is used as a humidifier, and the temperature of the heating device can be set to a range of, for example, 140° C. to 320° C. When the water is heated to the within the above range of temperatures, the water is vaporized and is rapidly and evenly dispersed in to the air. Naturally, the current supplied to the heating device may also be directly controlled so as to achieve the goal of controlling the temperature of the heating device. In some embodiments, the heating period of the heating device may be controlled according to a scent concentration or level that is desired by a user. Specifically, the user may set the heating device to intermittent heating, e.g., heat for 5 minutes or another time duration, within a larger interval of time (e.g., within each half hour, one hour, two hours, etc.). In some embodiments, a user may set the heating duration, particular times of day to turn on and to turn off, or adjust the scent concentration of the electronic scented candle as desired to provide the desired scent levels at appropriate times.

Referring back to FIGS. 4B and 5A, in some embodiments, the liquid suction channel 30 comprises a housing 31 and a liquid suction component 32. The liquid suction component 32 is disposed inside the housing 31, and an opening 33 is formed on the sidewall of the housing 31. The provision of the housing 31 enhances the mechanical strength of the liquid suction channel 30, which serves to extend the service life of the product, and also facilitates the installation of the liquid suction channel 30 into the fragrance container 10. The liquid in the fragrance container 10 can enter the liquid suction component 32 via the opening 33 formed at least partially on a bottom end of the sidewall of the housing 31, which ensures that substantially all of the liquid within the fragrance container 10 can be fully consumed by the liquid suction component 32 (see, for example, FIG. 4F illustrating that the liquid suction channel 30 extends to the very bottom of the fragrance container 10). The liquid suction component 32 may comprise an absorbent and high temperature-resistant material, such as absorbent cotton to allow the fragrance material to rise rapidly from the bottom end of the liquid suction channel 30 to its top. The fragrance material is then rapidly volatilized at the top end of the liquid suction channel 30 and dispersed into the external environment.

In addition, the liquid suction channel 30 has an elongated shape that extends beyond the fragrance material level (see, e.g., FIG. 4F illustrating the end of the liquid suction channel 30 extends into the scent chamber 20). As such, the fragrance material will not immediately fill up the entire length of the liquid suction channel after the liquid suction channel is placed into the fragrance material. This feature enables a user to install the liquid suction channel with ample time to avoid leakage of the fragrance material from the top end of the liquid suction channel 30. In one embodiment, the length of the liquid suction component 32 is greater than the length of the housing 31. As such, the liquid suction component 32 can be independently extended into the fragrance material, which in turn ensures that the liquid suction channel 30 fully absorbs the fragrance material of the container.

In some embodiments, the housing 31 and the liquid suction component 32 have the same length, as shown in, for example, FIGS. 5A and 5C-5E. In this configuration, the bottom of the housing 31 is provided with an opening 33, which, as noted earlier, ensures that the entire fragrance material is consumed. Moreover, it prevents a situation in which the fragrance material is pushed too quickly onto the liquid suction component 32 to cause overflow at the other end of the liquid suction channel 30. In some embodiments, as shown in, for example, FIGS. 4B, 4C and 5A, the liquid suction component 32 includes an absorbent cotton stick. A heating wire 41 can be wound at one end of the liquid suction component 32 (e.g., the absorbent cotton), as shown, for example, in FIG. 5B, which is an enlarged view of area B of FIG. 5A. This configuration has a simple structure and facilitates production and manufacturing of the components.

Figure 5B:
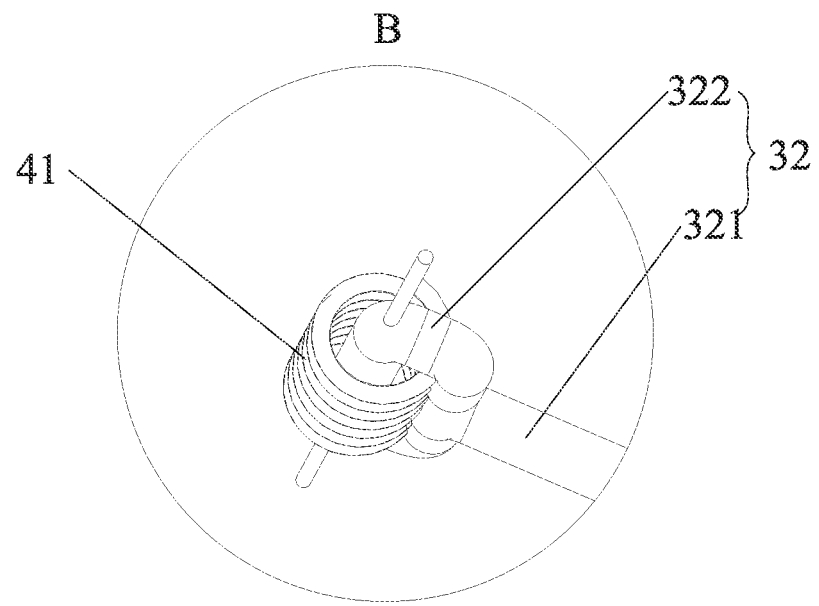
FIG. 5B illustrates an enlarged view a section of FIG. 5A.
Figure 5C:
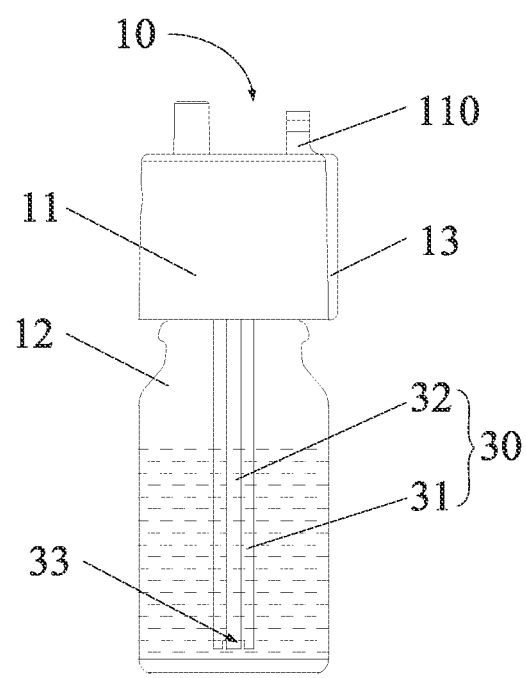
FIG. 5C illustrates a fragrance container in an upright position in accordance with another exemplary embodiment.
Figure 5D:
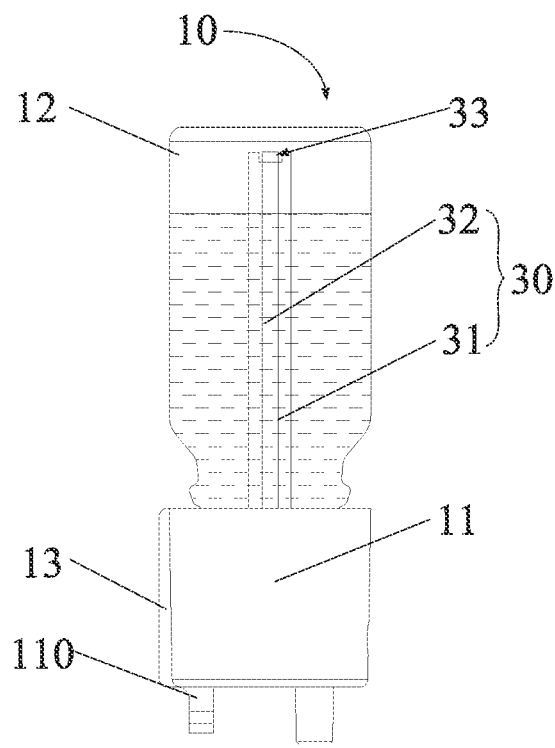
FIG. 5D illustrates a fragrance container in an upside down position in accordance with an exemplary embodiment.
Figure 5E:
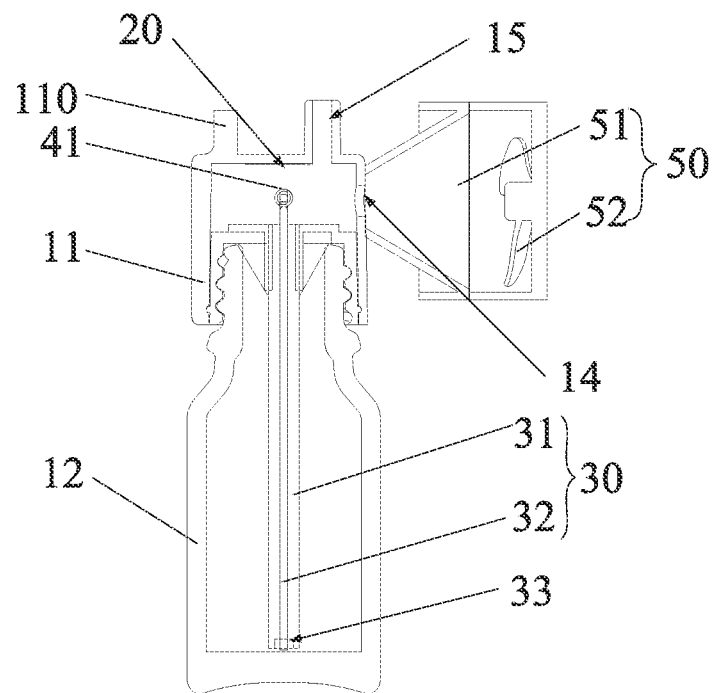
FIG. 5E illustrates a cross-section view of a fragrance container sand an air intake assembly in accordance with another exemplary embodiment.
Figure 5F:
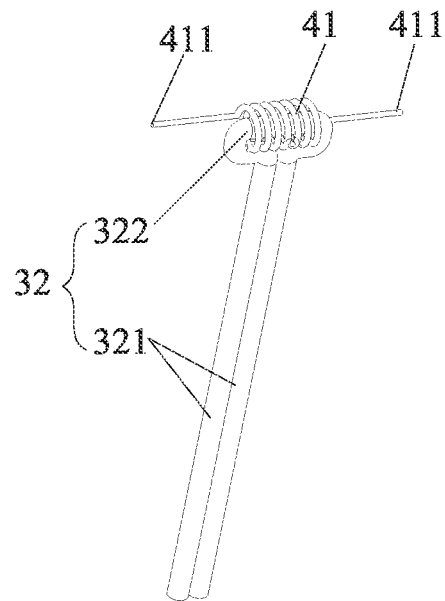
FIG. 5F illustrates sections of a heating wire and a liquid suction part in accordance with an exemplary embodiment.

In another embodiment, as shown in, for example, FIG. 5F, the liquid suction component 32 includes a folded section comprising an absorbent (e.g., cotton) material. The heating wire 41 is wound at the folded section of the absorbent material. This structure enables the liquid suction component 32 to rapidly absorb the fragrance material, thus enabling the electronic scented candle 300 to quickly release the scent into the outside environment. In one example, the liquid suction component 32 is formed by folding an absorbent cotton stick in half; in some implementations, the liquid suction component 32 may be formed by folding the absorbent cotton stick asymmetrically. It should be noted that, in some implementations, the heating wire 41 may not be disposed on the liquid suction channel 30, but can be positioned in its vicinity to heat up the liquid suction channel 30.

In some embodiments, as shown in, for example, FIGS. 4B and 5A, the cover body 11 of the fragrance container 10 is provided with a fixed bracket 16. An electrically conductive sheet(s) (elements 42 in FIG. 4B and elements 421 in FIG. 5A) is disposed on the fixed bracket 16. The fixed bracket 16 isolates the electrically conductive sheet(s) and prevents them from being exposed to the fragrance material, thus avoiding the corrosion of the conductive sheets and increasing their useful life.

As noted earlier and as shown, for example, in FIGS. 4D, 4E and 5C to 5E, in some embodiments, an opening 33 is formed at the bottom of the housing 31 of the liquid suction channel 30. When the fragrance container 10 is turned upside down (as shown in, e.g., FIG. 4E), the top level of the fragrance material in the bottle body 12 remains at a lower level than the opening 33, thus preventing the entry of the fragrance material into the liquid suction component 32 and thus preventing the unwanted leakage of the fragrance material.

In some embodiments, as shown in, for example, FIGS. 1D, 2B, 4F, and 5E, the electronic scented candle 300 further comprises an air supply assembly 50 disposed inside the electronic scented candle 300 for delivering air to air inlet 14. The air supply assembly 50 can increase the air flow, which in turn accelerates volatilization of the fragrance material for dissemination into the external environment. In addition, the air flow can be directed toward the scent outlet (e.g., the hole in the top middle section of the candle device) to cause the flame piece 170 swing irregularly. Such an irregular swing more closely resembles the flickering of a real flame.

In some embodiments, as shown in, for example, FIGS. 1D, 2B, 4F, and 5E, the air supply assembly 50 comprises a hood 51 and a fan 52; the air intake of the hood 51 is in communication with external air and the air outlet thereof is in communication with air inlet 14. The fan 52 is disposed inside the hood 51. The hood 51 guides the wind blown by the fan 52 toward the air inlet 14, and ensures that the air is completely guided into the air inlet 14, which in turn facilitates rapid volatilization of the fragrance material and release of the scent into the external environment.

In some embodiments, when the electronic scented candle 300 (or its scent generation engine) is turned off, the heating device 40 is first deactivated while the fan 52 continues to work for a particular duration of time to maintain the delivery of air into the scent chamber 20. This way, the residual fragrance that may exist in the scent chamber 20 is blown out of the scent chamber 20, thereby reducing or eliminating oxidization of the components due to prolonged exposure to the fragrance material. In one embodiment, the air supply assembly 50 further comprises a noise-reducing member to reduce the noise produce due to the operation of the fan 52.

In some embodiments, as shown in, for example, FIGS. 1D, 2B, 4F, and 5E, the diameter of the hood 51 tapers from the air intake to the air outlet 14; for example, the hood 51 is funnel shaped to cause the air that flows out of the hood 51 to have a relatively high velocity. The increased rate of air flow accelerates volatilization of the fragrance material at the top of the liquid suction channel 30, and facilitates rapid dissemination of the fragrance material into the external environment.

In some embodiments, the electronic scented candle further comprises a filter assembly. The filter assembly can absorb relatively large liquid droplets. As such, the filter assembly eliminates or reduces the amount of fog particles that may exit the scented candle while allowing the volatilized fragrance particles and air to reach the external environment.

In some embodiments, the electronic scented candle further comprises a smoke generation device to produce smoke that is blown out of the scent outlet via the air supply assembly. The blowing smoke can resemble the natural smoke associated with a real candle flame. The combination of smoke and illumination from one or more light-emitting elements produces a lifelike dynamic simulation that resembles a real fire flame.

In some embodiments, as shown in, for example, FIGS. 4B and 5A, the electronic scented candle 300 further comprises a sealing gasket 70 disposed inside the cover body 11 and located between the cover body 11 and the bottle body 12. The sealing gasket 70 is preferably made of PP (Polypropylene), rubber or silica gel, which produces a good seal and improves the tightness of installation between the cover body 11 and the bottle body 12, thereby reducing the vibrations of the cover body 11 and the associated noise. As shown in FIG. 5A, the housing 31 and the sealing gasket 70 can be formed as an integral unit to ensure the mechanical strength of the product, while at the same time reducing the number of required components which facilitates the manufacturing of the device and lowers its production costs.

Figure 6A:
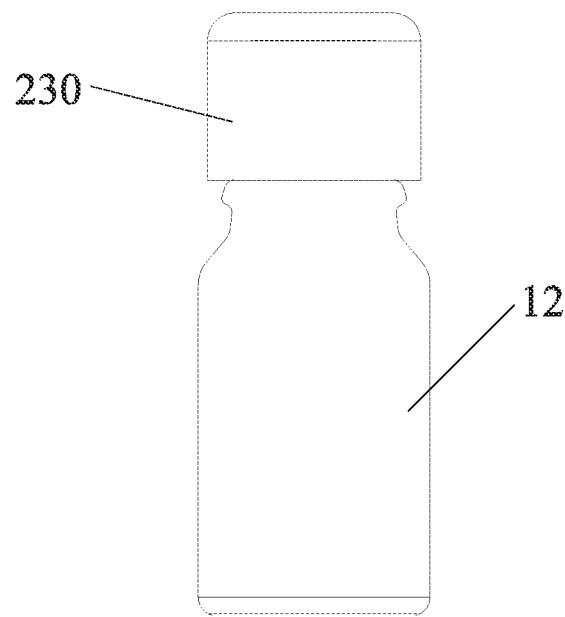
FIG. 6A illustrates a fragrance container in accordance with another exemplary embodiment.
Figure 6B:
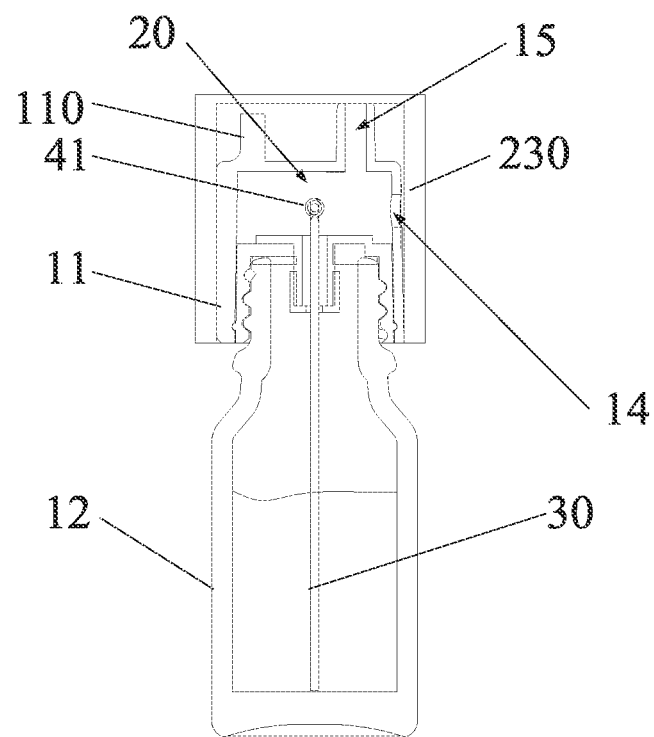
FIG. 6B illustrates a cross-sectional view of the fragrance container shown in FIG. 6A.

In some embodiments, as shown in, for example, FIGS. 6A and 6B, the electronic scented candle 300 further comprises a protective lid 230 that covers the cover body 11. Prior to installation of the fragrance container 10 in the electronic scented candle 300, the protective lid 230 can prevent evaporation of the fragrance material. A fragrance container 10 equipped with the protective lid 230 can be sold separately to allow a user to separately purchase the containers as needed.

In some embodiments, as shown, for example, in FIG. 1C, the electronic scented candle 300 further comprises an electric receptacle for connection to a power supply. In some embodiments, the receptacle can include a magnet that attracts another magnet that is embedded as part of a power cord 220 or an external power supply. When connection to a power source is needed, for example, to charge the batteries of the scented candle, the power cord 220 can be moved to the vicinity of the receptacle. The attractive force of the magnets can then assist in moving the power cord to properly mate with the receptacle. When the battery 310 is fully charged or the electronic scented candle 300 is not in use, the power cord 220 can be disconnected and removed from view. The magnetic member of the receptacle can be a magnet or an electromagnet that interacts with the magnet on the power cord 220, or may be made of a material, such as iron, that allows the magnet of the power cord 220 to be attracted to, and thus move toward, the receptacle.

Figure 2A:
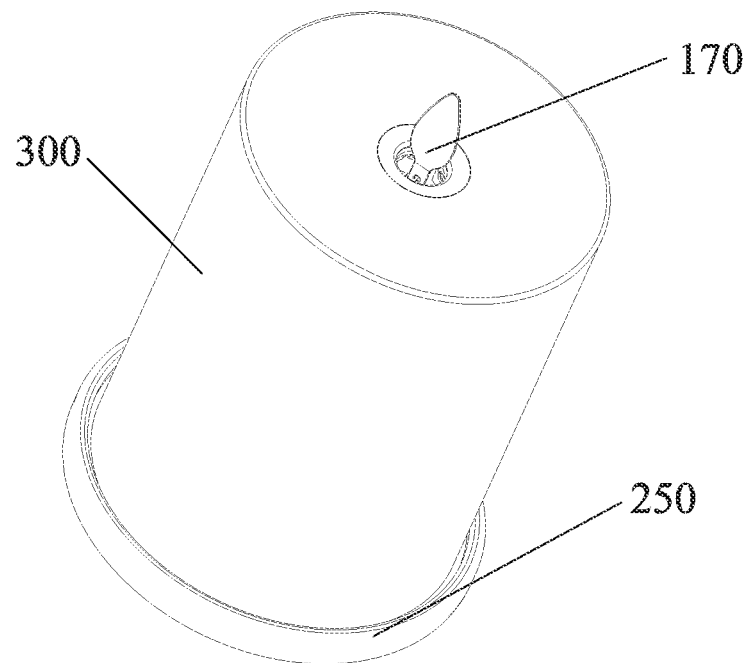
FIG. 2A illustrates an electronic scented candle according to an exemplary embodiment that includes a charging base.

In some embodiments, as shown, for example, in FIG. 2A, the electronic scented candle 300 further comprises a charging base 250 that allows a user to place the electronic scented candle 300 on the charging base 250 for charging. In some implementations, the charging base 250 is shaped to resemble a candlestick, which further enhances the resemblance of the candle device to a real candle. In a specific embodiment, the battery 310 is a lithium battery with a capacity of 3200 mAh. The battery 310 can typically be fully charged after 1.5 to 2 hours of charging. In other embodiments, the electronic scented candle 300 may be powered by a dry cell, an external power supply, or other power sources. In a specific embodiment, as shown in, for example, FIG. 1C, the power cord 220 is directly attached to the electronic scented candle 300 and forms an integral structure with the electronic scented candle 300.

Figure 2B:
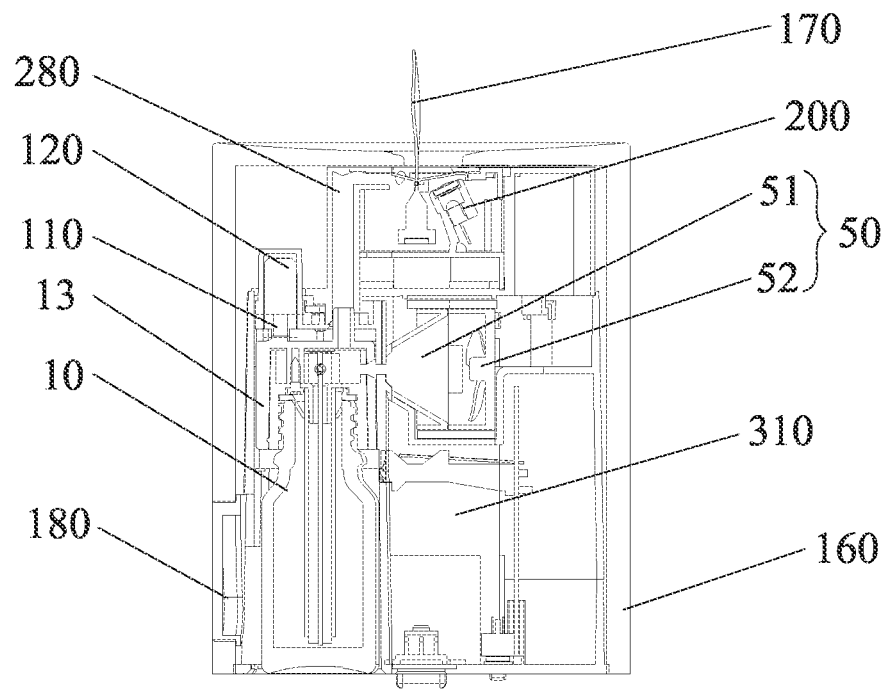
FIG. 2B illustrates a cross-sectional view of the electronic scented candle of FIG. 2A.

In some embodiments, as shown in, for example, FIG. 2B, the electronic scented candle 300 further comprises a scent discharge channel 280 disposed inside the shell and in communication with the scent outlet and the vent hole. The provision of the scent discharge channel 280 prevents the scent from entering other parts of the candle device and prevents corrosion of those parts. A corrosion-proof layer is provided on the inner wall of the scent discharge channel 280, which prevents or reduces corrosion of the scent discharge channel 280. Additionally or alternatively, the scent discharge channel 280 itself may be made of a corrosion-resistant material, such as PP (Polypropylene).

Figure 9A:
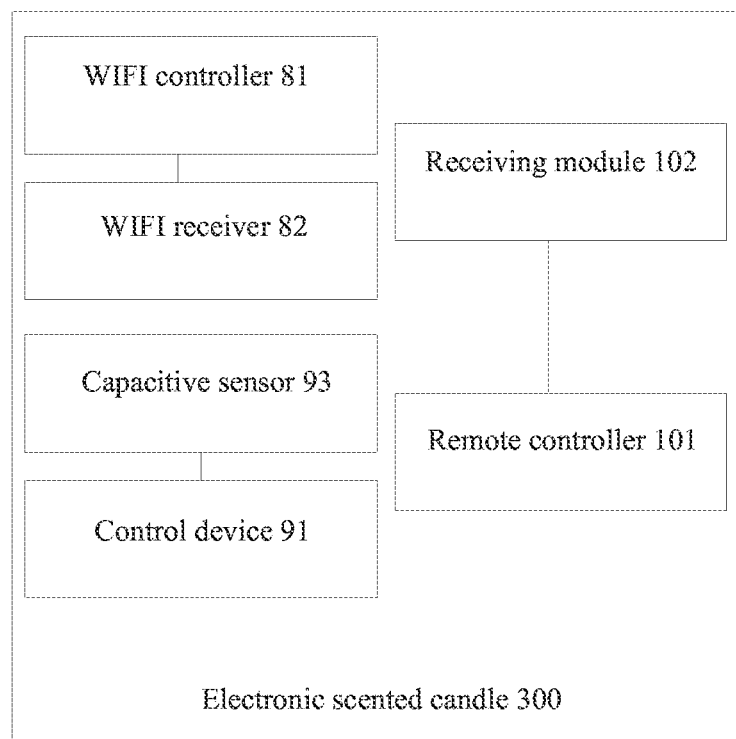
FIG. 9A is a schematic diagram of some of the components of an electronic scented candle in accordance with an exemplary embodiment.
Figure 9B:
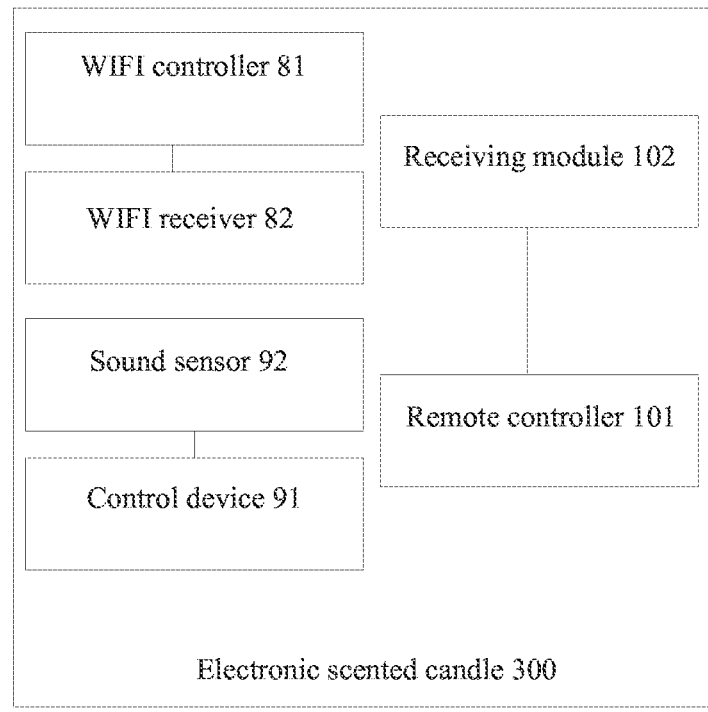
FIG. 9B is a schematic diagram of some of the components of an electronic scented candle in accordance with an exemplary embodiment.

In some embodiments, as shown, for example, in FIGS. 9A and 9B, the electronic scented candle 300 further comprises a WiFi controller 81 and a WiFi receiver 82. Specifically, the WiFi controller 81 is used to control one or more operations of the electronic scented candle 300. The WiFi receiver 82 is used to receive wireless signals and convert the received wireless signals into electric signals, which are input into the WiFi controller 81. The signals provided over a wireless network can be generated by a mobile terminal that runs an application (APP) to issue commands and instructions to the WiFi receiver 82, which receives those instructions via the wireless network, converts the instructions into an electric signal, and communicates them to the WiFi controller 81. The WiFi controller 81 controls, in turn, an operation of the electronic scented candle 300, such as to turn-on, turn-off, activate different modes of operation, set timers, etc. The APP on the mobile terminal can also display information regarding the operational state of the electronic scented candle 300. The mobile terminal can, for example, be a cell phone, a tablet computer, or a laptop computer.

In some embodiments, as shown, for example, in FIG. 9A and FIG. 9B, the electronic scented candle 300 further includes a control device 91 and a sensing element (92, 93). The control device 91 is used to control an operation of the electronic scented candle 300. The sensing element (91, 92) is used to receive an external input and convert the received external input into an electric signal, which is provided to the control device 91. The sensing element (91, 92) can for example receive an external signal or stimulus, such as a sound, air flow and pressure, a touch, a movement, etc., and convert the external signal into an electric signal that causes the control device 91 to control an operation of the electronic scented candle 300. For example, a user may, via voice control or pressure control, control various operations of the scented candle device, such as to turn it on and off, to set different operational modes, or set timer operations. Alternatively or additionally, the user can blow (or direct an airflow using a fan) to the sensor element to cause the electronic scented candle's flame to be "blown out" or extinguished by the fan. In this scenario, the control device 91 receives the signals associated with the detection of the blow or air flow, and can extinguish the "flame" of the electronic scented candle 300. At the same time, the control device 91 can control the smoke device to produce smoke to simulate the smoke produced when a real candle is extinguished.

Figure 2C:
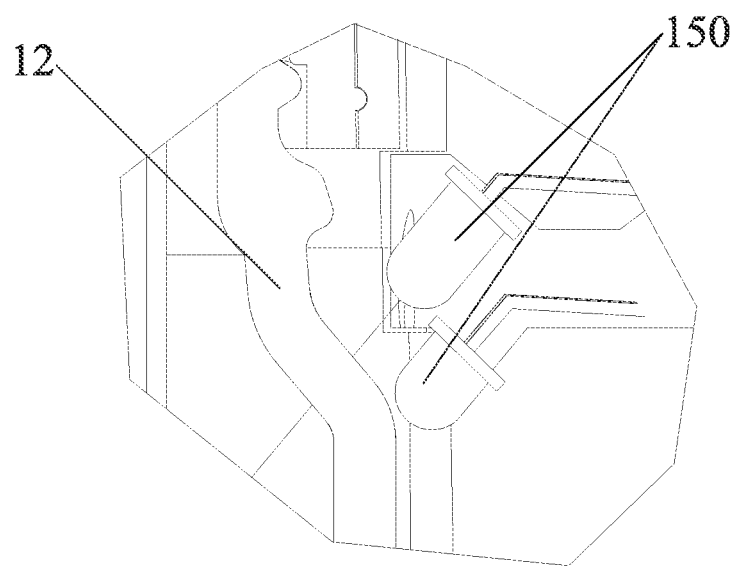
FIG. 2C illustrates an enlarged view of a section of scented candle of FIGS. 2A and 2B.
Figure 2D:
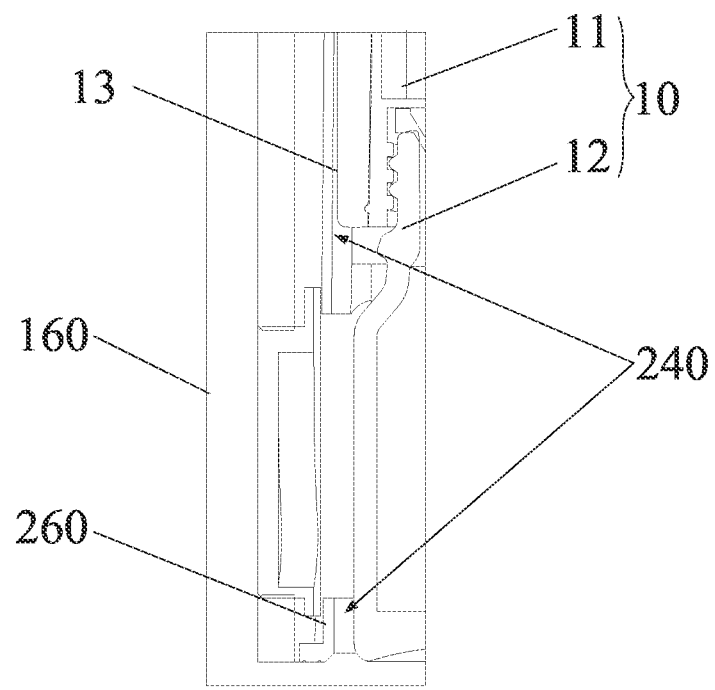
FIG. 2D illustrates an enlarged cross-sectional view of a section of the electronic scented candle of FIG. 2A.
Figure 2E:
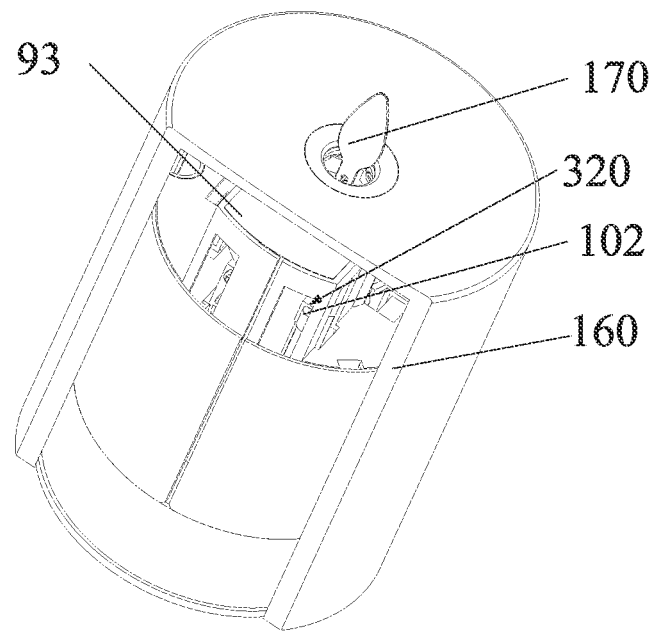
FIG. 2E illustrates another cross-sectional view of the electronic scented candle shown in FIG. 2A.

In some embodiments, as shown, for example, in FIG. 2E and FIG. 9A, the sensing element is a capacitive sensor 93. When a user touches the electronic scented candle 300, the capacitance of the capacitive sensor 93 changes, and the change in capacitance is converted to an electric signal that is input into the control device 91. In such embodiments, a user may control an operation of the electronic scented candle 300 by touching it. In particular, the user can touch or knock on the shell 160, which causes the capacitance of the capacitive sensor 93 to change and produce an electric signal. The control device 91 receives the electric signal and controls, according to the signal, an operation of the electronic scented candle 300, such as to turn in on or off, activate different modes of operation, set timer values, etc. For example, the user can knock on the shell 160 once to turn on the electronic scented candle 300, and knock the shell 160 again to turn the electronic scented candle 300 off. Knocking the shell 160 continuously can activate the timers, and a touch that persists for a long time (e.g., for more than a predetermined duration) can activate the setting of a operational modes. The control of the electronic scented candle 300 by means of touching has the following advantages: it allows the electronic scented candle to maintain an appearance of a natural candle (by eliminating the need for implementation of visible switches, knobs, etc.) while allowing different operational modes to be activated by simply touching an outside area of the candle device. Existing candle systems typically provide a control switch at the bottom of the electronic scented candle 300, which forces the user to pick up the candle device to control the operation of the candle. The capacitive sensor 93 may be disposed at different positions on the electronic scented candle 300. In some embodiments, the capacitive sensor 93 is disposed on the external surface of the electronic scented candle 300, and the surface of the capacitive sensor 93 is provided with a non-metal layer. The material of the non-metal layer can the same as the material of the shell 160, such as wax/plastic, so as to ensure the consistency and elegance of the electronic scented candle 300. The sensing element may also be a pressure sensor that can be used to sense pressure or force that is excreted on the candle device, and convert the pressure to an electric signal for input to the control device 91.

In some embodiments, as shown, for example, in FIG. 9B, the sensing element is a sound sensor 92 that is used to respond to a sound wave, and convert the sound wave into an electric signal that is provided to the control device 91. A user may control an operation of the electronic scented candle 300 by using voice. For example, the sound sensor 92 can receive a sound wave (e.g., a word or a phrase uttered by the user) and convert the sound wave to an electric signal that is used by control device 91 to control an operation of the electronic scented candle 300, such as to turn the candle on/off, set timers, and so on. In one example, the user can activate the electronic scented candle 300 using a voice command, such as ""Hello Scent" or "Hello Candle", or initiate a particular operation of the electronic scented candle 300 via a voice command, such as "Turn on the scent." In response, the sound sensor 92 captures the sound wave associated with the voice comment and controls the operation of the heating device 400 to, e.g., turn on the scent feature of the electronic scented candle 300. In another example, a user can inquire: "Check the current state of the scent", in response to which, the control device 91 can provide feedback regarding the current scent-releasing rate of the fragrance. In yet another example, the user can ask: "Set a scent", in response to which the control device 91 can adjust the current scent-releasing level of the fragrance. For example, the user may directly say "high scent," "medium scent," or "low scent" to request the appropriate levels of scent release. In still another example, the user tells the electronic scented candle 300 "Turn off the scent", in response to which the control device 91 turns off the heating device 400 of the electronic scented candle 300.

It should be understood that the above description regarding voice control of the scent feature is one example of various voice control operations that can be implemented in accordance with the disclosed embodiments. In some example embodiments, the sound sensor 92 is a microphone, as shown in, for example, FIG. 1A. The microphone can be disposed above the observation window 180, or disposed on top surface of the shell 160. In other examples, the microphone can be disposed at a position to the right or left of the flame piece of the electronic scented candle 300 (e.g., inside the top central hole on top of the candle device). In such a configuration, the flame piece can hide the microphone from plain view, which makes the appearance of the candle device closer to a real candle. Moreover, a sound wave can be immediately captured by the microphone, thereby ensuring the reliability and speed of actions that are initiated by the voice commands. In some embodiments, the control circuitry within the electronic scented candle 300 are capable of recognizing and reacting to a plurality of languages, such as Chinese, English, Japanese, Korean, etc. In some embodiments, during the voice interaction between a user and the electronic scented candle 300, the electronic scented candle may provide feedback to the user via voice. In such embodiments, the electronic scented candle 300 includes a power amplifier circuit and a loudspeaker therein to enable such a feedback.

In some embodiments, as shown in, for example, FIGS. 2E, 9A and 9B, the electronic scented candle 300 further comprises a remote controller 101 that is coupled to a receiving module 102. The receiving module 102 receives commands and signals from a remote control (not shown), converts them to electrical signals and communicates them to the remote controller 101 to control various operations of the electronic scented candle 300, such as to turn the candle device on/off. The mode of signal transmission by the remote control may be carried out via infrared, Bluetooth, high-frequency module, and other wireless transmission technologies. In some embodiments, the electronic scented candle 300 is provided with a notch 320 (see, e.g., FIG. 2E) at the position near the receiving module 102. Alternatively, the shell of the receiving module 102 can be made of a transparent or translucent material so as to allow the receiving module 102 to receive signals from all angles. In some embodiments, remote control can have 10 touch keys: Touch Key 1 turns the product on/off; Touch Keys 2 to 4 can correspond to high, medium and low fragrance concentration (high-speed volatilization of fragrance (high), mid-speed volatilization of fragrance (mid), and low-speed volatilization of fragrance (low)), respectively; Touch Keys 5 to 7 can correspond to different durations of heating device operation, e.g., 120 min, 180 min, 240 min working duration, respectively; Touch Keys 8 to 10 can correspond to different durations for operation of the light-emitting devices, e.g., 6 hours, 8 hours, and 10 hours, respectively. A user may set the duration for the heating device 40, the light-emitting elements 200 according to specific requirements.

Figure 7A:
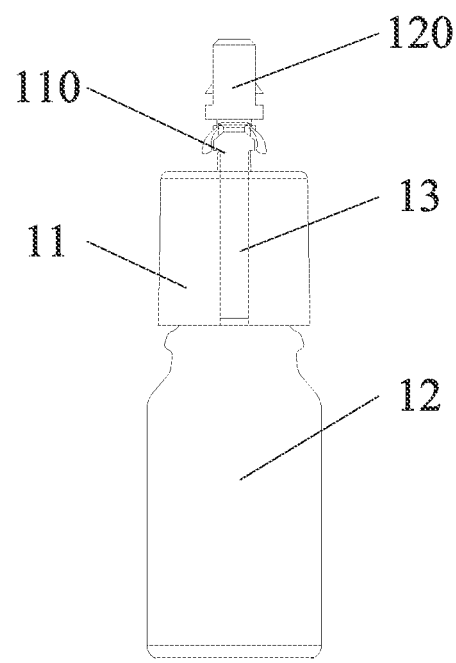
FIG. 7A illustrates sections of the fragrance container and an associated slot in accordance with an exemplary embodiment.
Figure 7B:
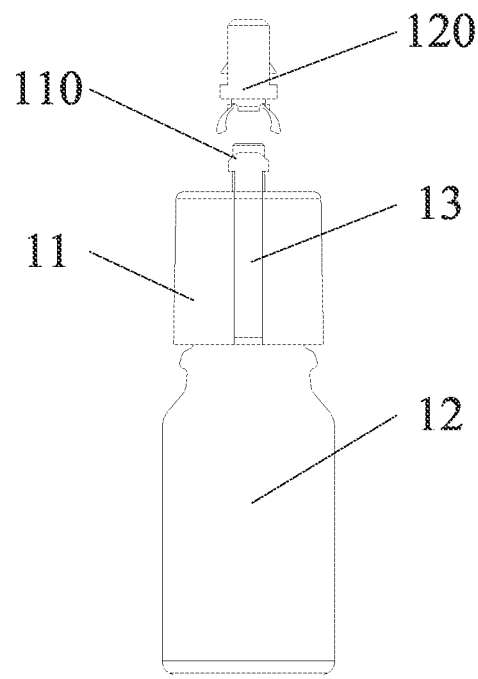
FIG. 7B illustrates an exploded view of the structure shown in FIG. 7A.

In some embodiments, as shown in, for example, FIGS. 1D, 2B, 4A, 6B, 7A, and 7B, the fragrance container 10 is provided with a buckle 110 on the cover body 11. The buckle 110 is in snap connection with the wall of the installation chamber. In some embodiments, the installation chamber includes a slot 120 that engages the buckle 110. Specifically, the cover body 11 includes a buckle 110 that can be disposed at the top or on a side of the cover body 11; the slot 120 is formed at a position so as to engage with the buckle 110. In one embodiment, the slot 120 is formed on the installation chamber and preferably formed integrally with the installation chamber. In an example embodiment, as shown in FIG. 4A, the buckle 110 has a structure similar to T that is wide on its top and narrow on its bottom. In another embodiment, as shown in FIGS. 7A and 7B, the slot 120 is shaped as key.

Figure 8A:
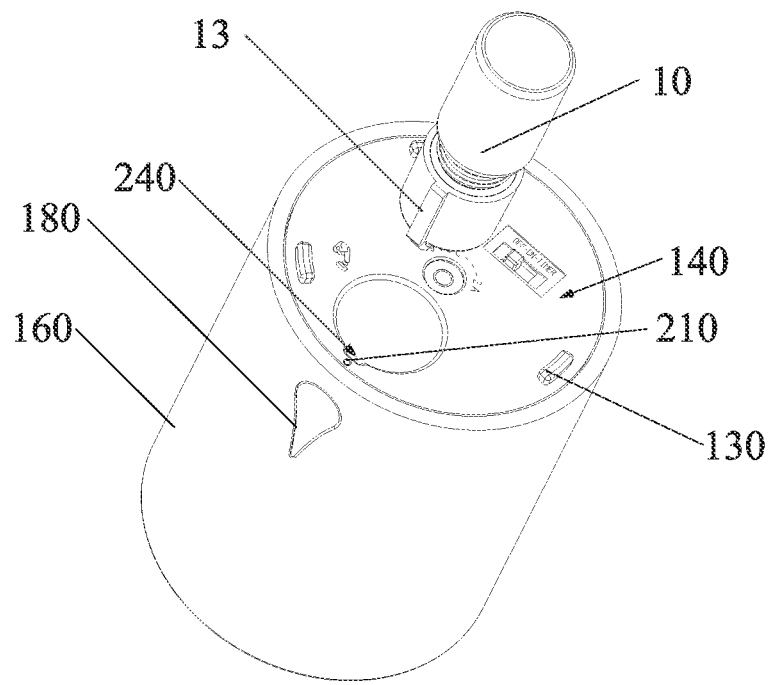
FIG. 8A is a first diagram illustrating the insertion of a fragrance container into an electronic scented candle in accordance with an exemplary embodiment.
Figure 8B:
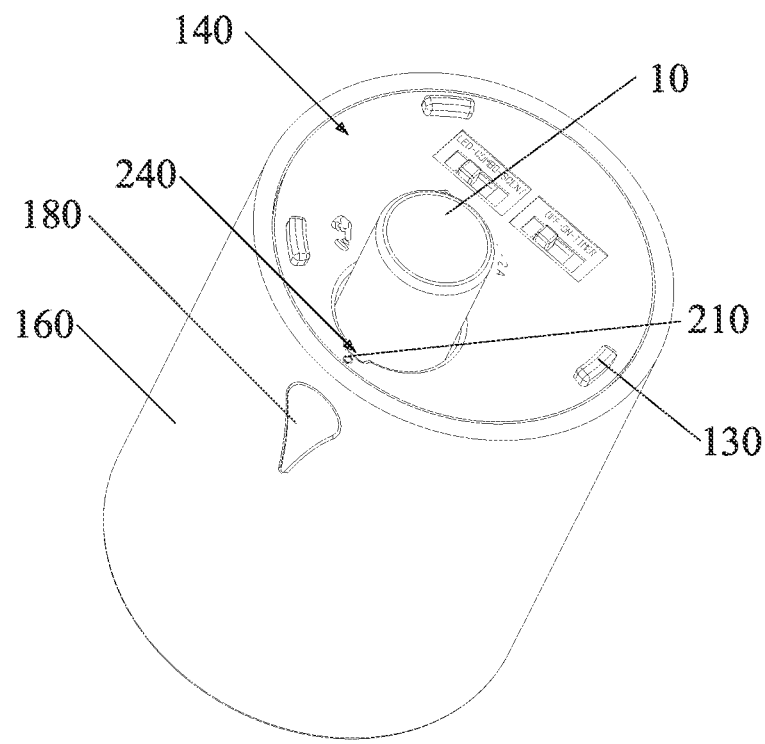
FIG. 8B is a second diagram illustrating the insertion of a fragrance container into an electronic scented candle in accordance with an exemplary embodiment.
Figure 8C:
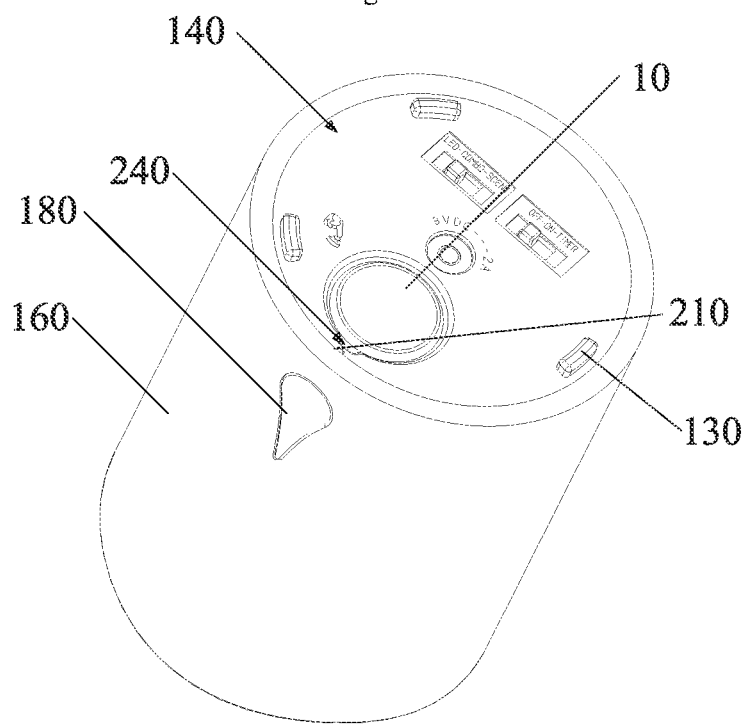
FIG. 8C is a third diagram illustrating the insertion of a fragrance container into an electronic scented candle in accordance with an exemplary embodiment.

FIGS. 8A to 8C illustrate a process for installation of the fragrance container 10 into the electronic scented candle 300. In particular, as illustrated in FIG. 8A, the fragrance container 10 is inserted into pushed into the installation chamber from the bottom of the electronic scented candle 300 and pushed until it snaps into the slot 120. If a user wants to take out the fragrance container 10, the user may touch and press the bottom of the fragrance container 10, which causes the cover body 11 installed with the fragrance container 10 to disengage from the slot 120. In other embodiments, the cover body 11 can be snapped into the slot 120 through the buckle 110; when the fragrance container 10 needs to be replaced, the fragrance container 10 may be rotated at an angle such that the cover body 11 installed with the fragrance container 10 disengages from the slot 120.

In some embodiments, as shown in FIG. 4B, FIG. 5A, and FIG. 5F, the heating device 40 comprises a heating wire 41 and two electrically conductive sheets 42; the heating wire 41 is wound around the liquid suction channel 30; one end of the two electrically conductive sheets 42 is connected to the connection end 411 of the heating wire 41, respectively; the other end thereof is connected into a power supply circuit of the electronic scented candle 300 (i.e. one end of one of the electrically conductive sheets is connected to one end of the heating wire, the other end thereof is connected into a power supply circuit of the electronic scented candle, one end of the other electrically conductive sheet is connected to the other end of the heating wire, and the other end thereof is connected into the power supply circuit of the electronic scented candle). After the fragrance container 10 is installed into the electronic scented candle 300, the two electrically conductive connectors 42 are connected into a power supply circuit of the electronic scented candle 300. After the electronic scented candle 300 is powered on, the heating wire 41 heats up by being powered on through the two electrically conductive connectors 42. The heating wire 41 heats the liquid suction channel 30 to accelerate the volatilization of the fragrance, and the scent is volatilized from the scent outlet into the external air such that the electronic scented candle 300 can release a scent. In some embodiments, the other end of the electrically conductive connectors 42 projects beyond the cover body 11, and a pin in engagement with the electrically conductive connectors 42 is provided inside the installation chamber. When the fragrance container 10 is installed into the installation chamber, the electrically conductive connectors 42 press against the pin, and at this moment, the buckle 110 is snapped into the slot 120, and the fragrance container 10 is locked. When the fragrance container 10 is to be removed from the electronic scented candle 300, the pin is compressed, which provides, together with the door lock switch, a force for the ejection of the fragrance container 10, such that the fragrance container 10 is fully ejected. In some embodiments, the electrically conductive connectors 42 are U shaped, and the pin can be inserted into the electrically conductive connectors 42, such that the pin is in full contact with the electrically conductive connectors 42. Naturally, the electrically conductive connectors 42 may also formed as sheets, and the pin can rest against the plane of the electrically conductive connectors 42. Those skilled in the art should understand that the electrically conductive connectors 42 may have any shape, as long as they can be in contact with the pin. In some embodiments, as shown in FIG. 5A and FIG. 5B, the heating wire 41 is wound around the liquid suction component 32. Alternatively, the liquid suction component 32 can be wound around the heating wire 41. The liquid suction component 32 comprises an absorptive section 321 and a winding section 322, and the heating wire 41 is wound around the winding section 322. Alternatively, the winding section 322 can be wound around the heating wire 41. Moreover, the liquid suction component 32 can be divided into two parts. In some embodiments, a user may replace the absorptive section 321 when, for example, different fragrances are used. This way, the mixture of different scents can be avoided. In some implementations, the heating wire 41 can be an iron-chromium-aluminum electric heating wire, a nickel-chromium electric heating wire, or a copper-based alloy electric heating wire.

In some embodiments, as shown in FIG. 5A, the electrically conductive connectors 42 comprises sheet bodies 421 and connection poles 422. The sheet body 421 is disposed inside the cover body 11. One end of the connection pole 422 extends beyond the cover body 11 and can be connected into a power supply circuit of the electronic scented candle 300. The other end thereof is connected with the sheet body 421. In some embodiments, the electrically conductive connectors 42 can be divided into two parts, and the two parts can be first installed separately, and then assembled, leading to a convenient assembly procedure. The connection pole 422 and the cover body 11 can be integrally injection-molded. In particular, the electrically conductive connectors 42 and the top cover body 11 can be integrally injection-molded such that there is no gap between the connection pole 422 and the cover body 11. As a result, volatilization of an evaporated fragrance from between the cover body 11 and the connection pole 422 is avoided, thus improving the sealing properties of the device. In some configurations, a sealing member may be used between the electrically conductive connectors 42 and the cover body 11 for sealing purpose; the sheet body 421 can be welded to the connection end 411 of the heating wire 41. In some embodiments, the electrically conductive connectors 42 may only include the connection poles 422 that are connected to the heating wire 41 that is connected to the power supply circuit.

In some embodiments, as shown in FIG. 4A, FIG. 7A, and FIG. 7B, a limit projection 13 is formed on a side of the cover body 11. As shown in FIG. 8A through FIG. 8C, the wall of the installation chamber of the electronic scented candle 300 is formed with a limit groove 240, and the limit projection 13 engages with the limit groove 240 to allow the fragrance container 10 to be installed at a fixed angle when positioned into the installation chamber. Such a mechanism improves the ease of installation. As for example shown in FIG. 8A through FIG. 8C, the limit projection 13 that is positioned on the cover body 11 makes it impossible to install the fragrance container 10 into the electronic scented candle 300 if the limit projection 13 is not aligned with the limit groove 240. Therefore, the engagement between the limit projection 13 and the limit groove 240 enables the fragrance container 10 to be smoothly and accurately installed into the electronic scented candle 300, and at the same time, prevents incorrect installation of the fragrance container 10. In addition, as shown in FIG. 8A through FIG. 8C, a guide point 210 may be provided on the bottom of the electronic scented candle 300 to prompt a user to align the limit projection 13 with the prompt point 210 to further enable smooth and accurate installation of the fragrance container 10. In some embodiments, as shown in FIG. 8A through FIG. 8C, the limit groove 240 extends to the base of the electronic scented candle, and the cover body 11 and the bottle body 12 have the same diameter. During installation of the fragrance container 10, the limit groove 240 is visible, and a user can directly align the limit projection 13 with the limit groove 240, such that the fragrance container 10 is smoothly and accurately installed into the electronic scented candle 300. At the same time, due the present of the guide point 210, the user incorrect installation of the fragrance container 10 is avoided. In some embodiments, the base is provided with a projection 260 (see FIG. 2D) that extends into the electronic scented candle 300, and a part of the limit groove 240 is formed on the projection 260. The projection 260 adds to the overall strength of the base, and at the same time allows the limit groove 240 to have a relatively long length.

In some embodiments, the cover body 11 and the fragrance container 10 to the electronic scented are fixedly attached to the candle 300 through a snap-connection structure. In some embodiments, the cover body 11 and the fragrance container 10 are fixedly attached to the electronic scented candle 300 through a door lock switch. It should be understood, however, that other connections mechanisms can also be used for connecting the cover body 11 and the fragrance container 10 to the electronic scented candle 300.

In some embodiments, the base of the electronic scented candle 300 is provided with a plurality of support components 130 that are spaced apart from each other (see FIGS. 1A and 1C). As shown in FIG. 1B and FIG. 1C, the base of the electronic scented candle 300 includes an opening to allow the power cord 220 of the electronic scented candle 300 to be connected to the power supply through the opening. The power cord 220 may extend out of the electronic scented candle 300 via the spacing 140 between the bottom surface of the candle 300 and the surface upon which it rests. The adjacent support components 130 can further limit the movement of the power cord 220 such that the power cord 220 can only move within the space defined by the spacing 140 and the separation between the adjacent support components 130. The user can position the cord between any two of the support components 130 to allow a desired orientation of the candle and the power cord 220 that extends out below the candle.

In some embodiments, as for example, shown in FIG. 1D and FIG. 8C, there is a gap 60 between the fragrance container 10 and the wall of the installation chamber. The air inlet 14 is in communication with the external air through the gap 60, and the gap 60 can be used as an air supply channel. In operation, as the fan 52 drives the air to flow into the air inlet 14, the air enters the scent chamber 20 from the air outlet, while air is replenished through the air inlet through the gap 60, which ensures that the air is promptly replenished into the scent chamber 20, such that the fragrance is volatilized rapidly into the external air and the electronic scented candle 300 can release a scent rapidly. In some embodiments, the electronic scented candle 300 is provided with an independent air supply channel, such as an intake port 270 (see FIG. 3A) that is formed on the base of the electronic scented candle 300. The intake port 270 is formed on the inner side of the support components 130, and the support components 130 can block the intake port 270 from view to ensure an elegant appearance of the electronic scented candle 300. Alternatively, as shown in FIG. 3B, the intake port 270 can be formed at center of the base of the electronic scented candle 300.

In some embodiments, as shown for example in FIG. 1A through FIG. 1D and FIG. 2B, the shell 160 is provided with an observation window 180 thereon. The observation window 180 is constructed to allow at least some of the contents of the fragrance container 10 to be visible. The shell 160 of the electronic scented candle 300 is provided with at least one observation window 180 thereon, (when there is a plurality of fragrance containers 10, a plurality of observation windows 180 may be correspondingly disposed to allow the contents of each fragrance container 10 to be viewed). This way, a viewer can visually assess how much of the fragrance material is remaining in the fragrance container 10. In some embodiments, the profile of a receiving hole on the wall of the installation chamber opposing the observation window 180 is greater than the profile of the observation window 180, which, on one hand, prevents a user from seeing the hole wall of the receiving hole and ensures an elegant appearance of the product, and on the other hand, lowers the difficulty in installation of an observation window 180 and improves the production efficiency of the product. In one embodiment, the observation window 180 is made of a clear plastic; in other embodiments, the observation window 180 may be a hole of a specific shape, including but not limited to any one of a rectangle, a rhombus, an ellipse, a water droplet, or a combination thereof. As shown in FIG. 8A through FIG. 8C, in some embodiments, the limit groove 240 and the observation window 180 are provided within the side of the candle device. The observation window 180 can be placed at the appropriate location on the shell 160, which has a relatively large surface area. As such the observation window 180 will not obscure or interfere with other components of the candle device. Moreover, the height of the projection 260 can be selected to be lower than the position of the observation window 180, so as to ensure that the projection 260 is not seen through the observation window 180.

Figure 1E:
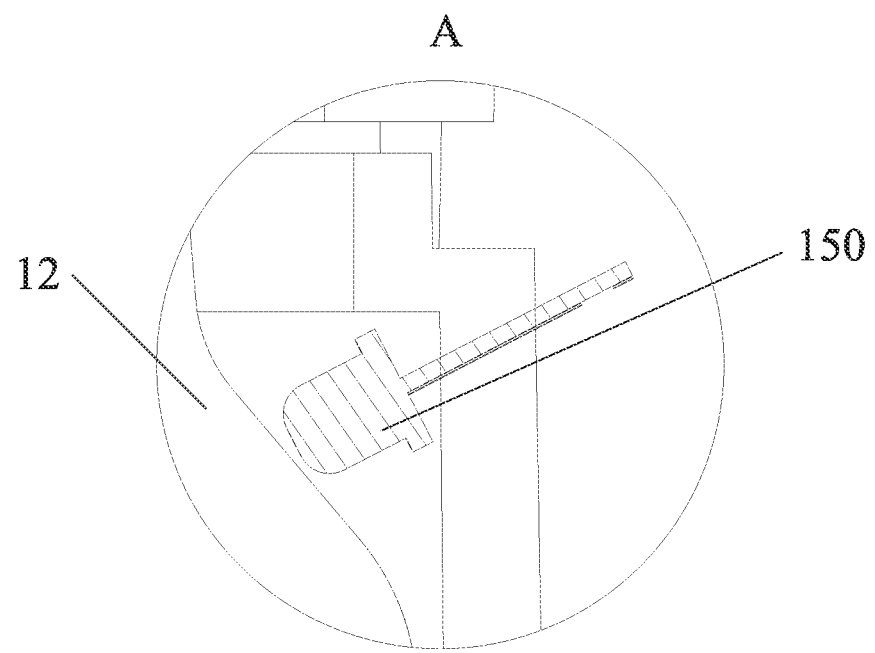
FIG. 1E illustrates an enlarged view of a section of the electronic scented candle of FIG. 1D.

In some embodiments, as shown in for example FIG. 1E and FIG. 2C, the electronic scented candle 300 further comprises a light source 150. The light source 150 is disposed close to the observation window 180 for illuminating the fragrance container 10. The light source 150 can illuminate the bottle body 12 of the fragrance container 10 such that the amount of fragrance material remaining in the container can be seen even in dark ambient environments. The light source 150 is preferably disposed on the shell 160, but may be disposed in other locations in the electronic scented candle 300. The light source 150 may be an LED lamp. In some embodiments, the electronic scented candle 300 further comprises a controller. The controller is connected with the light source and controls the light source and displays a status of the electronic scented candle 300. For example, when the battery 310 of the electronic scented candle 300 is in a charging state, the light source 150 is on, and the light source 150 is turned on having a particular color. When the battery 310 is fully charged, the light source 150 provides illumination in another color. For example, when the battery 310 is in a charging state, the light source 150 provides a red color; when the battery 310 is 50% charged, the light source 150 turns yellow; and when the battery 310 is fully charged, the light source 150 turns white. In addition, the light source 150 may also function as a signal indicator. For example, when a sensor receives a signal, the light source 150 flickers to prompt a user that the electronic scented candle 300 has received a signal. In some embodiments, when a user operates the candle device while the candle is being charged, the light source operation is prioritized to give a higher priority to the touch display operation, and can automatically switch to the providing the charging-specific signals at a particular time interval (e.g., three seconds) after the user stops the operation. In addition, as shown in FIG. 2C, there may be one or more light sources 150. In one example, when the battery 310 of the electronic scented candle 300 only has 20% power left, the light source is turned in red color to prompt a user to promptly charge the device (in case of a rechargeable battery) or to replace with a new battery (in case of a dry cell).

It should be noted that embodiments of the present application show examples that there is one fragrance container 10, but variations of embodiments of the electronic scented candle 300 of the present invention can be implemented to include a plurality of fragrance containers 10, e.g. two, three or more fragrance containers 10. In one embodiment, the electronic scented candle 300 includes a plurality of scent chambers 20, where one fragrance container 10 is connected to one scent chamber 20. In another embodiment, one scent chamber 20 is connected to a plurality of fragrance containers 10. In other embodiments, the electronic scented candle 300 includes one scent chamber 20 and a plurality of fragrance containers 10 that are connected to the scent chamber 20. In configurations with a plurality of fragrance containers 10, a user chooses his/her favorite fragrances for combination and mixing, thereby producing a mixed scent or "concoction" in his/her own way to even produce scents that never existed before. In one embodiment, the scents from the plurality of fragrance containers 10 may all be directed into one scent chamber 20 and then discharged from one scent outlet. In another embodiment, the scents from the plurality of fragrance containers 10 may all be directed into a plurality of scent chambers 20, respectively, and then to an external environment of the electronic scented candle 300 from a plurality of scent outlets. In such a way, different scents can either be mixed before being delivered to an external environment, or first be sent to an external environment and then mixed in the air, both of which can further improve the diversity and mixing effect of scents.

In some embodiments, as shown in for example FIG. 1A, FIG. 1D, and FIG. 2A, the upper portion of the electronic scented candle 300 is preferably provided with a flame piece 170 in the form of a flame shape, which is capable of making irregular movements. When a light is projected onto the flame piece 170, the flame piece 170 randomly sways to produce a similar effect as a real flame. In addition, the flame piece 170 can include a black section to simulate a real candle wick. The black section is positioned outside of the installation hole of the electronic scented candle 300 to simulate a wick of a real candle after burning. Along with the flickering of the flame piece 170, the electronic scented candle 300 releases a scent at the same time, which can create a desired (e.g., romantic) atmosphere. The upper portion of the flame piece 170 is preferably formed as a sheet-like flame piece, or may be combined by two or more sheet-like flame pieces, or may even be a 3-dimensional component. In some embodiments, the flame piece 170 may be made of plastic or an organic synthetic material. In one preferred embodiment, the flame piece 170 is made of a translucent material, such that the flame can be seen from both sides of the flame piece 170. In another preferred embodiment, the upper portion of the flame piece 170 has an uneven thickness, e.g., thin at the top and thick at the bottom, or thin at the top, thick in the middle, and thin at the bottom, to simulate different lighting effects of a flame at different heights and to improve the life-like appearance of the flame. In one embodiment, the lower portion of the flame piece 170 has a magnet or a magnetic material, such that the light-emitting elements 200 can undergo nonlinear movements that vary with time under the action of the magnetic field. In another embodiment, the flame piece 170 is driven in another mode such due to a air flow produced by a fan or an airflow from the outside environment.

In some embodiments, as shown in FIG. 1D and FIG. 2B, one or more light-emitting elements 200 may be provided, such that light is directly or indirectly projected onto the flame-shaped elements on the upper portion of the flame piece 170 from one or more light-emitting element 200. In some embodiments, an optical element, such as lens, may be used to simulate the flame in a more life-like manner. The light-emitting element 200 may be an LED light source. The LEDs may be installed at one side of the flame piece 170, the LEDs may be installed at two sides of the flame piece 170, or the LEDs may be installed at the bottom of a stand that supports the flame piece 170. The light-emitting element 200 may also be a halogen lamp.

As shown in FIG. 1A and FIG. 2A, the shell 160 of the electronic scented candle 300 is preferably constructed to have a shape similar to a conventional candle. The cross section of the shell 160 may be further formed to have a triangular, square, oval or irregular shape. Paths may be formed on the shell 160 that look like solidified flows of melted wax, so as to simulate a used candle. The shell 160 may be made of materials including wax, paraffin, plastics, glass, metal, ceramic, crystal, polymers, or any combination thereof. The top of the electronic scented candle 300 may be substantially a flat surface to simulate a brand-new unused candle, or to include a recessed top surface to simulate a candle that has been used for a period. The top of the electronic scented candle 300 is formed with an installation hole, and the flame piece 170 extends outwardly from inside the shell 160 via the hole. In one embodiment, the installation hole on the top of the electronic scented candle 300 is the same hole as the scent outlet. In other embodiments, the scent outlet may be formed separately, for example, on the side or bottom of the electronic scented candle 300. There may also be a plurality of scent outlets to allow the scent to be rapidly diffused into the air.

In some embodiments, the electronic scented candle further comprises a tilt sensor (not shown). The tilt sensor is constructed to shut down the power supply to the heating device when the electronic scented candle is tilted by a predetermined angle. In such a way, when the electronic scented candle is tilted, the tilt sensor can sense such an action and then shut down the power supply to the heating device. When the electronic scented candle is tilted or placed upside down, the heated fragrance would flow out of the fragrance container and to the heating device or a circuit of the electronic scented candle. By shutting down the power supply to the heating device in such a case, short circuit of the power supply is avoided thus improving the safety of the of the candle device. In one embodiment, an angle threshold is set for tilting; for example, the threshold angle can be set at 45° or 75° with respect to the vertical axis of the electronic scented candle. The tilt sensor determines the tilt angle of the candle and shuts down the power supply when the tilt angle equals or exceeds the threshold angle. In one embodiment, three tilt sensors are arranged in a triangle with the angle therebetween to be 45° or 75°. In this configuration, when the vertical axis of the electronic scented candle forms an angle of 45° or 75° relative to the vertical state, the power supply to the heating device is shut down. In one embodiment, the tilt sensor may be a ball switch. In addition, when the electronic scented candle 300 is down, the function of the electronic scented candle 300 is immediately shut down, and the light source 150 keeps on flashing in red until the product is put back in its position, when the electronic scented candle 300 is restored to the state and settings prior to the shutdown.

The electronic scented candle further comprises a power supply including a battery chamber that accommodates one or more dry cells or rechargeable batteries. In the case of a rechargeable batteries, the batteries can be charged in a wireless charging mode; alternatively or additionally, the batteries may be charged with solar energy that is converted into electrical energy for storage when the product is not in use. In another embodiment, the power supply may include a plug that is directly connected to AC at home or work so as to supply power to the electronic scented candle.

In some embodiments, the fragrance container 10 may be present in the electronic scented candle 300 when the product leaves the factory. In some other embodiments, the electronic scented candle 300 may not carry the fragrance container 10 when leaving the factory, and instead, a user may install it on his/her own into the installation chamber according to his/her preferences.

Figure 3A:
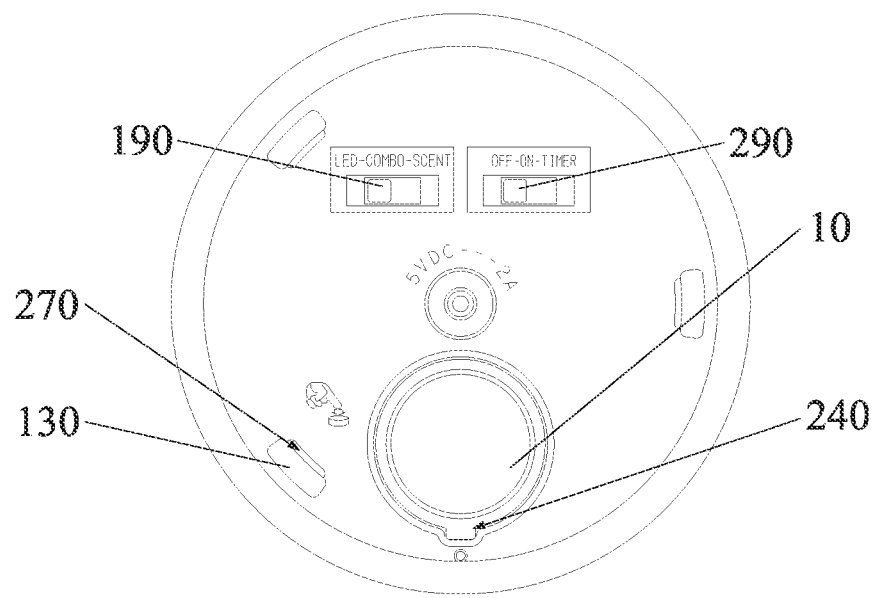
FIG. 3A illustrates a bottom view of an electronic scented candle in accordance with an exemplary embodiment.
Figure 3B:
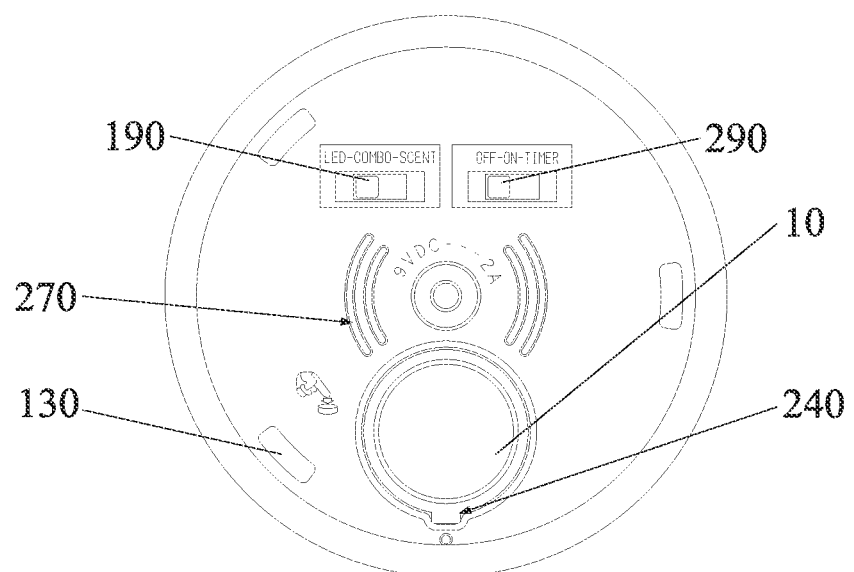
FIG. 3B illustrates a bottom view of an electronic scented candle in accordance with another exemplary embodiment.

In some embodiments, as shown for example in FIG. 3A and FIG. 3B, the bottom of the electronic scented candle 300 is provided with a plurality of toggle switches. For example, a first switch 190 includes three switch positions: LED, Combo, and Scent. A second switch 290 includes three switch positions: Off, On, and Time. The first switch 190 and the second switch 290 are disposed at the bottom of the electronic scented candle 300, which ensures the overall elegant appearance of the electronic scented candle 300. Since the electronic scented candle 300 includes support components 130, the height of the first switch 190 and the second switch 290 can be selected slightly protrude from the bottom surface of the shell 160 (but no more than the height of the support components 130) to facilitate their operations by a user.

An exemplary operation control of the electronic scented candle 300 using the above noted switched is as follows:

1. When the first switch 190 is pushed to the LED position, the heating device 40 is not turned on. Upon detection by the capacitive sensor 93 that a user has touched the electronic scented candle 300, in the case of one touch, the light-emitting element 200 is turned on. If another touch is detected, the light-emitting element 200 is turned off. If a constant touch for three seconds is detected, and if the second switch 290 is at the On position, a five-hour timer is activated, and the light-emitting element 200 flashes once to indicate that the timer has been activated. If the second switch 290 is at the Time position and a constant touch for three seconds is detected, the light source 150 turns on with the white color, and stays on for three seconds, which also activated the timing setting mode. The initial default timer setting of the electronic scented candle 300 is five hours. When the timer is set for five hours, the light-emitting element 200 flashes once, the light source 150 turns to white and stays on for three seconds. When the light source 150 turns to white and stays on, each touch would change to a different timer duration: one touch activates a six-hour timer and the light-emitting element 200 flashes twice; one more touch activates an eight-hour timer and the light-emitting element 200 flashes three times; a further touch activates a five-hour timer and the light-emitting element 200 flashes once, and the cycle can be repeated in similar manner. After three seconds of no touches, the light source 150 turns to white and turns off while the timer is set according to the last touch. If a user wants to reactivate the timer after the light source 150 turns off, the user needs to apply a continuous touch for three seconds, at which time the light-emitting element 200 will flash for a number of times corresponding to the currently-set timer value. The light source 150 turns to white and stays on for three seconds, indicating that the timer mode is entered to allow the operations to be repeated as described above.

2. When the first switch 190 is pushed to the Scent position, the light-emitting element 200 is turned off. Upon detection of a touch by the capacitive sensor 93 of the electronic scented candle 300, in the case of one touch, the heating device 40 is turned off. If an additional touch is sensed, the heating device 40 is turned on and the light source 150 turns to white and stays on for one second. The default initial scent state of the electronic scented candle 300 is low-speed volatilization of fragrance. In case of sensing of a continuous touch for three seconds, if the second switch 290 is at the On position, a 120 minute timer state is entered, the light source 150 turns to white and flashes once, indicating that the timer is activated. When the second switch 290 is at the Time position, the timer setting mode is entered after continuous touch for three seconds is detected. The default timer duration is, for example, 120 minutes. If then current timer state is 120 minutes, the light-emitting element 200 flashes once, and when the light source 150 turns to white and stays on, each touch would change to a different timer duration. For example, one touch activates a 180 minute timer and the light-emitting element 200 flashes twice. One additional touch activated a 240 minute timer and the light-emitting element 200 flashes three times. An additional touch activates a 120 minute timer and the light-emitting element 200 is activated to flash once, and the cycle can be repeated in a similar manner. After three seconds of no operation, the light source 150 turns off with the last touch having determined the final timer state. If a user wants to reactivate the timer after the light source 150 turns off, the user needs to apply a continuous touch for three seconds, at which time the product will display the current timing state, and the light source 150 will flash for a number of times corresponding to the current timing state. The light source 150 turns to white and stays on for three seconds, indicating that the timer setting mode is entered, and the cycle can be repeated in a similar manner.

3. When the first switch 190 is pushed to the Combo position, the light-emitting element 200 and the heating device 40 work simultaneously. Upon detection of a touch by the capacitive sensor 93, in the case of one touch, the heating device 40 is turned off, and in the case of sensing an additional touch, the heating device 40 is turned on and the light source 150 turns to white and stays on for one second. The default initial scent state of the electronic scented candle 300 is low-speed volatilization of fragrance. When a continuous touch for three seconds is sensed, if the second switch 290 is at the On position, a five-hour timer state is entered, the light-emitting element 200 flashes, indicating that timer is activated. When the second switch 290 is at the Time position, the timer setting mode is entered after a continuous touch for three seconds is detected; the light source 150 stays on for three seconds. The initial default timer value of the electronic scented candle 300 is five hours. If the current timer state is five hours, the light-emitting element 200 flashes once. When the light source 150 is white, each touch would change the timer setting to a different timer duration. For example, one touch activates a six-hour timer and the light-emitting element 200 flashes twice. An additional touch activates an eight-hour timer and the light-emitting element 200 flashes three times. A further touch activates a five-hour timer and the light-emitting element 200 flashes once, and the cycle can be repeated in a similar manner. After three seconds of no operation, the light source 150 turns to white and turns off with the last touch having determined the final timer setting. If a user wants to reactivate the timer after the light source 150 turns off, the user needs to apply a continuous touch for three seconds to activate the timer mode; the light-emitting element 200 will flash for a number of times corresponding to then current timer setting, and at the same time, the light source 150 turns to white and stays on for three seconds, indicating that the timer setting mode is entered, and the cycle can be repeated in a similar manner.

The Low (i.e., low-speed volatilization of fragrance) mode of the electronic scented candle 300 has the following initial settings: the heating device 40 has a current of 300 MA, and every 2 minutes of heating is followed by 15 minutes of pause. The Mid (i.e., mid-speed volatilization of fragrance) mode has the following initial settings: the heating device 40 has a current of 320 MA, and every 2 minutes of heating is followed by 15 minutes of pause. The High (i.e., high-speed volatilization of fragrance) mode has the following initial settings: the heating device 40 has a current of 350 MA, and every 2 minutes of heating is followed by 15 minutes of pause.

The above control mode is an example of one embodiment; additional operational modes can be implemented consistent with the disclosed embodiments.

Another aspect of the disclosed embodiments relates to a fragrance container 10 comprising a cover body 11, a bottle body 12, a heating device 40, a liquid suction channel 30, an electric energy input end, and a scent chamber 20. The scent chamber 20 is disposed on the cover body 11, and the cover body 11 covers the bottle body 12. An air inlet 14 and a vent hole 15 of the scent chamber 20 are in communication with external air (the external air refers to the air outside of the fragrance container 10). One end of the liquid suction channel 30 extends into a fragrance material in the bottle body 12, whereas the other end of the liquid suction channel 30 extends into the scent chamber 20. The liquid suction channel 30 is capable of sucking fragrance from one end of the liquid suction channel 30 to the other end thereof. A heating device 40 is disposed inside the scent chamber 20 for heating one end of the liquid suction channel 30. One or more electrical connectors are disposed on the cover body 11 and are connected with the heating device 40. The electrical connectors can comprise an electrically conductive sheet 42.

With respect to the fragrance container, a liquid in the bottle body rises from the bottom to the top of the liquid suction channel due to capillary action. The heating device is powered on and heats the liquid suction channel to accelerate volatilization (or vaporization) of the fragrance. The scent is volatilized from the scent outlet into the external air to release the scent. Heat can accelerate the movement speed of molecules, and the heated fragrance molecules can move into the air rapidly, such that the fragrance container can quickly produce a scent after being powered on. This mode of scent dissemination is faster relative to existing configurations that rely on rapid air flow disperse a scent.

In the description of the present invention, it should be understood that orientation or position relationship indicated by terms such as "up", "down", etc., is an orientation or position shown in the accompanying drawings (see, e.g., FIG. 1A), which is provided only for facilitating the description of the present invention and for simplifying the description.

The invention claimed is:

1. An electronic scented candle, comprising:
  a shell having a cylindrical shape and including a top surface that is substantially flat, the top surface further including a hole;
  a movable component that extends outwardly from inside the shell through the hole, the movable component having an upper portion that is formed as a three-dimensional flame-shaped structure, a lower portion of the movable component including a magnet;
  a light source to illuminate the upper portion of the movable component that is formed as three-dimensional flame-shaped structure;
  a fragrance container insertable within the shell in an installation chamber, wherein the installation chamber is cylindrical in shape having a smaller cross-sectional diameter than the shell and having a longitudinal axis that is offset from a longitudinal axis that passes through a center of the shell, the fragrance container being insertable into the installation chamber through a bottom of the electronic scented candle;
  a scent chamber within the shell above the fragrance container and coupled to the fragrance container for receiving a fragrance material from the fragrance container;
  an air inlet connected to the scent chamber to allow air to be directed into the scent chamber;
  a cylindrical channel positioned within the fragrance container, the cylindrical channel having a first end at a top section of the fragrance container to allow access to the scent chamber and a second end positioned inside the fragrance container;
  an electric fan positioned within the shell and configured to drive the air into the scent chamber;

a scent outlet coupled to the scent chamber to allow the fragrance material to leave the scent chamber; and a receptacle for connecting a power cord to the electronic scented candle, the receptacle positioned on a bottom surface of the electronic scented candle, the bottom surface further including a plurality of stands that protrude from the bottom surface, the plurality of stands allowing the electronic scented candle to be placed upon a surface while providing a space between the bottom surface of the electronic scented candle and the surface upon which the electronic scented candle is placed, wherein the space allows the power cord to be connected to the receptacle and be routed below the bottom surface.

2. The electronic scented candle of claim 1, comprising a sealing gasket positioned to, upon insertion of the fragrance container into the installation chamber, form a seal between the fragrance container and the scent chamber.

3. The electronic scented candle of claim 2, wherein the sealing gasket comprises a material that includes one of a polypropylene, rubber or silica gel.

4. The electronic scented candle of claim 1, wherein the scent outlet is coupled to the hole on the top surface of the shell to allow the fragrance material to exit the electronic scented candle.

5. The electronic scented candle of claim 1, wherein the scent outlet is formed separately from the top hole on the top surface of the shell to allow the fragrance material to exit the electronic scented candle.

6. The electronic scented candle of claim 5, wherein the scent outlet is formed on a side or bottom of the electronic scented candle.

7. The electronic scented candle of claim 1, further including a heater coupled to the scent chamber to facilitate dissemination of the fragrance material.

8. The electronic scented candle of claim 7, wherein the heater is configured to operate at a temperature between 150° C. to 350° C.

9. The electronic scented candle of claim 1, wherein the cylindrical channel is configured to draw the fragrance material into the scent chamber.

10. The electronic scented candle of claim 9, wherein the cylindrical channel comprises an absorbent material.

11. The electronic scented candle of claim 1, further comprising a remote controller coupled to a receiver that resides inside the shell, the remote controller configured to transmit electromagnetic signals to the receiver for controlling an operation of the electronic scented candle.

12. The electronic scented candle of claim 11, wherein the electromagnetic signals include infrared signals.

13. The electronic scented candle of claim 1, wherein the shell is formed of a translucent material.

14. The electronic scented candle of claim 1, wherein the three-dimensional flame-shaped structure is formed of a translucent material.

15. The electronic scented candle of claim 1, further comprising a switch positioned on the bottom surface, wherein the switch allows timed operation of the electronic scented candle for a predetermined duration of time.

16. The electronic scented candle of claim 15, wherein the switch is a three-position toggle switch.

17. The electronic scented candle of claim 15, wherein the predetermined duration of time is five hours.

18. The electronic scented candle of claim 1, wherein the receptacle includes a magnet that attracts another magnet that is embedded as part of the power cord.

19. The electronic scented candle of claim 1, wherein the receptacle is positioned at one of a side or a center location of the bottom surface.

20. The electronic scented candle of claim 1, wherein the electronic scented candle is operable to simultaneously induce movements of the movable component and illumination of the upper portion of the movable component that is formed as the three-dimensional flame-shaped structure while disseminating the fragrance material.

21. The electronic scented candle of claim 1, further including a tilt sensor configured to sense that the electronic scented device is tilted by a predetermined angle and to disconnect a power source of the electronic scented device in response thereto.

22. The electronic scented candle of claim 1, wherein light from the light source is directly projected onto at least a portion of the upper portion of the movable component that is formed as the three-dimensional flame-shaped structure.

23. The electronic scented candle of claim 1, wherein the light source is a light emitting diode (LED).

24. The electronic scented candle of claim 1, further including one or more additional light sources positioned inside the shell.

25. The electronic scented candle of claim 24, wherein the one or more additional light sources are capable of producing light with different colors.

26. The electronic scented candle of claim 1, wherein the installation chamber includes a slot that is configured to engage a buckle on the fragrance container to allow the fragrance container to be snapped into place within the installation chamber.

27. An electronic scented candle, comprising:

a cylindrical shell formed from a translucent material, the shell comprising a top surface that includes a hole and a bottom surface that includes an opening that forms an entrance to an installation chamber;

a fragrance container comprising a fragrance material in liquid form, the fragrance container configured to be inserted into the installation chamber through the opening of the bottom surface, wherein the installation chamber is cylindrical in shape and has a smaller cross-sectional diameter than the shell, the installation chamber located at an offset position with respect to a longitudinal axis that passes through a center of the shell;

a movable component that extends outwardly from inside the shell through the hole, the movable component having an upper portion that is formed as a three-dimensional flame-shaped structure, a lower portion of the movable component including a magnet that resides within the shell;

a light source to illuminate at least a section of the upper portion of the movable component that is formed as the three-dimensional flame-shaped structure;

a scent chamber coupled to the fragrance container that is inserted into the installation chamber to receive a portion of the fragrance material from the fragrance container;

an air inlet coupled to the scent chamber to allow air to be directed into the scent chamber;

a scent outlet coupled to the scent chamber to allow the fragrance material to leave the scent chamber, the scent outlet including a conduit for allowing the fragrance material from within the scent chamber to be dispersed to an area outside of the electronic scented candle;

a cylindrical tube positioned vertically within the fragrance container, the cylindrical tube being at least partially immersed in the fragrance material of the fragrance container, the cylindrical tube extending to a top section of the fragrance container from one end and extending to a bottom section of the fragrance container from a second end;

an electric fan positioned within the shell and coupled to a power source, the electric fan configured to provide an airflow to the scent chamber and to force at least some of the fragrance material from within the scent chamber to the scent outlet;

a power receptacle on the bottom surface of the electronic scented candle configured to receive an end of a power cord, the bottom surface further including a plurality of stands that protrude from the bottom surface, the plurality of stands allowing the electronic scented candle to be placed upon a surface while providing a space between the bottom surface of the electronic scented candle and the surface upon which the electronic scented candle is placed, wherein the space allows the end of the power cord to be connected to the receptacle and the power cord to be routed below the bottom surface; and a receiver for receiving infrared signals from a remote controller for controlling an operation of the electronic scented candle, wherein the electronic scented candle is operable to simultaneously induce movements of the movable component and illumination of the three-dimensional flame-shaped structure while disseminating the fragrance material.

28. The electronic scented candle of claim 27, further including a heating element coupled to the scent chamber to increase a temperature of the scent chamber and to facilitate dissemination of the fragrance material in vapor form.

29. The electronic scented candle of claim 27, wherein the cylindrical tube is configured to transfer the fragrance material from the fragrance container to the scent chamber.

* * * * *